(12) United States Patent
Mumm et al.

(10) Patent No.: US 10,398,761 B2
(45) Date of Patent: Sep. 3, 2019

(54) METHODS OF USING COMBINATIONS OF PEG-IL-10 AND IL-15 FOR TREATING CANCERS

(71) Applicant: ARMO BioSciences, Inc., Redwood City, CA (US)

(72) Inventors: John Brian Mumm, Los Altos Hills, CA (US); Ivan Ho Chan, Millbrae, CA (US)

(73) Assignee: Armo Biosciences, Inc., Redwood City, CA (US)

( * ) Notice: Subject to any disclaimer, the term of this patent is extended or adjusted under 35 U.S.C. 154(b) by 0 days.

(21) Appl. No.: 15/751,134

(22) PCT Filed: Aug. 24, 2016

(86) PCT No.: PCT/US2016/048399
§ 371 (c)(1),
(2) Date: Feb. 7, 2018

(87) PCT Pub. No.: WO2017/035232
PCT Pub. Date: Mar. 2, 2017

(65) Prior Publication Data
US 2019/0030131 A1 Jan. 31, 2019

Related U.S. Application Data

(60) Provisional application No. 62/209,500, filed on Aug. 25, 2015.

(51) Int. Cl.
| | | |
|---|---|---|
| *A61K 38/20* | (2006.01) | |
| *A61K 45/06* | (2006.01) | |
| *A61K 33/24* | (2019.01) | |
| *A61K 47/60* | (2017.01) | |
| *A61P 35/00* | (2006.01) | |
| *A61K 9/00* | (2006.01) | |

(52) U.S. Cl.
CPC ........ *A61K 38/2086* (2013.01); *A61K 9/0019* (2013.01); *A61K 33/24* (2013.01); *A61K 38/2066* (2013.01); *A61K 45/06* (2013.01); *A61K 47/60* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 4,965,195 A | 10/1990 | Namen et al. | |
| 5,032,396 A | 7/1991 | Williams | |
| 5,229,115 A | 7/1993 | Lynch | |
| 5,231,012 A | 7/1993 | Mosmann et al. | |
| 5,252,714 A | 10/1993 | Harris et al. | |
| 5,328,989 A | 7/1994 | Vellekamp et al. | |
| 5,624,823 A | 4/1997 | Sachs et al. | |
| 5,643,575 A | 7/1997 | Martinez et al. | |
| 5,665,345 A | 9/1997 | Yarchoan et al. | |
| 5,696,234 A | 12/1997 | Zurawski et al. | |
| 5,705,149 A | 1/1998 | Namen et al. | |
| 5,710,251 A | 1/1998 | Vellekamp et al. | |
| 5,824,784 A | 10/1998 | Kinstler et al. | |
| 5,866,134 A | 2/1999 | Fine et al. | |
| 5,876,969 A | 3/1999 | Fleer et al. | |
| 5,908,621 A | 6/1999 | Glue et al. | |
| 5,919,455 A | 7/1999 | Greenwald et al. | |
| 5,932,462 A | 8/1999 | Harris et al. | |
| 5,945,097 A | 8/1999 | Cutler | |
| 5,951,974 A | 9/1999 | Gilbert et al. | |
| 5,985,263 A | 11/1999 | Lee et al. | |
| 5,985,265 A | 11/1999 | Kinstler et al. | |
| 5,985,857 A | 11/1999 | Kinstler et al. | |
| 5,989,867 A | 11/1999 | Knappe et al. | |
| 6,217,857 B1 | 4/2001 | Mosmann et al. | |
| 6,248,514 B1 | 6/2001 | Hutchins et al. | |
| 6,387,364 B1 | 5/2002 | Fersuson | |
| 6,428,985 B1 | 8/2002 | Bromberg et al. | |
| 6,660,258 B1 | 12/2003 | Tovey | |
| 6,685,931 B1 | 2/2004 | Grint et al. | |
| 6,770,272 B2 | 8/2004 | Strom et al. | |
| 6,989,377 B2 | 1/2006 | Hayes et al. | |
| 7,001,770 B1 | 2/2006 | Atencio et al. | |
| 7,052,684 B2 | 5/2006 | Ferguson | |
| 7,052,686 B2 | 5/2006 | Lee et al. | |
| 7,056,701 B2 | 6/2006 | Fleer et al. | |
| 7,261,882 B2 | 8/2007 | Watkins | |
| 7,462,351 B2 | 12/2008 | Conroy et al. | |
| 7,611,700 B2 | 12/2009 | Gantier et al. | |
| 7,650,243 B2 | 1/2010 | Gantier et al. | |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

"Guidance for Industry Immunogenicity Assessment for Therapeutic Protein Products," (2013) *FDA Guidances*.
"Highlights of Prescribing Information," (1997) *Rituxan*.
Abbasi, Amanullah, et al., (2012) "Serum Cholesterol: Could it be a Sixth Parameter of Child-Pugh Scoring System in Cirrhotics Due to Viral Hepatitis?", Journal of the College of Physicians and Surgeons Pakistan, 22(8):484-487.
Accession AAC23839.1; GI 3242896; Jun. 8, 2000.
Accession ABY86619.1; GI 166244598 ; Feb. 4, 2008.
Accession NP_001009327.1; GI 57164347; Feb. 13, 2011.

(Continued)

*Primary Examiner* — Elly-Gerald Stoica
(74) *Attorney, Agent, or Firm* — Robert Brian Johnson

(57) ABSTRACT

Methods of treating subjects having a cancer-related disease, disorder, or condition, or preventing the occurrence of such a disease, disorder or condition, via the administration of a PEG-IL-10 agent in combination with an IL-15 agent are provided.

20 Claims, 8 Drawing Sheets

Specification includes a Sequence Listing.

(56) References Cited

U.S. PATENT DOCUMENTS

| | | |
|---|---|---|
| 7,666,400 B2 | 2/2010 | Chang et al. |
| 7,749,490 B2 | 7/2010 | Sommer et al. |
| 7,939,056 B2 | 5/2011 | Horwitz et al. |
| 8,044,175 B2 | 10/2011 | Dransfield et al. |
| 8,067,532 B2 | 11/2011 | MacLean |
| 8,287,856 B2 | 10/2012 | Li et al. |
| 8,398,968 B2 | 3/2013 | Mayall |
| 8,618,256 B2 | 12/2013 | Cox |
| 8,691,205 B2 | 4/2014 | Blaisdell et al. |
| 8,697,045 B2 | 4/2014 | Lee et al. |
| 8,865,652 B2 | 10/2014 | Oft et al. |
| 9,238,079 B2 | 1/2016 | Lee et al. |
| 9,259,478 B2 | 2/2016 | Blaisdell et al. |
| 9,364,517 B2 | 6/2016 | Oft et al. |
| 2002/0012665 A1 | 1/2002 | Hanna |
| 2002/0044921 A1 | 4/2002 | Lee et al. |
| 2003/0012775 A1 | 1/2003 | Brandt et al. |
| 2003/0186386 A1 | 10/2003 | Hansen et al. |
| 2004/0101965 A1 | 5/2004 | Griesenbach et al. |
| 2004/0213795 A1 | 10/2004 | Collins et al. |
| 2005/0008615 A1 | 1/2005 | Bam et al. |
| 2005/0164352 A1 | 7/2005 | Lauder et al. |
| 2005/0260767 A1 | 11/2005 | Clerici et al. |
| 2006/0046961 A1 | 3/2006 | McKay et al. |
| 2006/0210534 A1 | 9/2006 | Lee et al. |
| 2006/0258607 A1 | 11/2006 | Jarosch et al. |
| 2006/0270041 A1 | 11/2006 | Howe et al. |
| 2007/0122379 A1 | 5/2007 | Nielsen et al. |
| 2007/0134197 A1 | 6/2007 | Eichner et al. |
| 2008/0058246 A1 | 3/2008 | Bhaskaran et al. |
| 2008/0069797 A1 | 3/2008 | Roncarolo et al. |
| 2008/0081031 A1 | 4/2008 | Oft et al. |
| 2008/0096252 A1 | 4/2008 | Zamost et al. |
| 2008/0107629 A1 | 5/2008 | LaFace et al. |
| 2009/0035256 A1 | 2/2009 | Sommer et al. |
| 2009/0048148 A1 | 2/2009 | Engler et al. |
| 2009/0214463 A1 | 8/2009 | Slobedman et al. |
| 2009/0214471 A1 | 8/2009 | Oft et al. |
| 2009/0311187 A1 | 12/2009 | Berman et al. |
| 2010/0068147 A1 | 3/2010 | Hibberd et al. |
| 2010/0111898 A1 | 5/2010 | Pelura |
| 2010/0129386 A1 | 5/2010 | Elson et al. |
| 2010/0255496 A1 | 10/2010 | Schrader et al. |
| 2010/0266532 A1 | 10/2010 | Ferguson |
| 2010/0297070 A1 | 11/2010 | Dugan et al. |
| 2011/0009589 A1 | 1/2011 | Harris et al. |
| 2011/0064690 A1 | 3/2011 | Lee et al. |
| 2011/0091419 A1 | 4/2011 | Oft et al. |
| 2011/0250163 A1 | 10/2011 | Blaisdell et al. |
| 2011/0275123 A1 | 11/2011 | Paciotti et al. |
| 2011/0305665 A1 | 12/2011 | Lee et al. |
| 2011/0312010 A1 | 12/2011 | Manuilov |
| 2012/0003221 A1 | 1/2012 | McDonagh et al. |
| 2012/0115926 A1 | 5/2012 | Geary et al. |
| 2012/0142033 A1 | 6/2012 | Fujiwara |
| 2012/0213793 A1 | 8/2012 | Huang et al. |
| 2012/0252742 A1 | 10/2012 | Kranz et al. |
| 2012/0270899 A1 | 10/2012 | Bannister et al. |
| 2012/0321617 A1 | 12/2012 | Osterroth et al. |
| 2013/0039911 A1 | 2/2013 | Bedi et al. |
| 2013/0156774 A1 | 6/2013 | Kuchroo et al. |
| 2014/0199750 A1 | 7/2014 | Weng et al. |
| 2014/0256626 A1 | 9/2014 | Santi et al. |
| 2014/0314795 A1 | 10/2014 | Riddell et al. |
| 2014/0349402 A1 | 11/2014 | Cooper et al. |
| 2015/0038678 A1 | 2/2015 | Eaton et al. |
| 2015/0118244 A1 | 4/2015 | Shahabi et al. |
| 2016/0193300 A1 | 7/2016 | Mumm et al. |
| 2016/0340406 A1 | 11/2016 | Zhao et al. |
| 2016/0361415 A1 | 12/2016 | Mumm et al. |
| 2016/0375101 A1 | 12/2016 | Oft |

FOREIGN PATENT DOCUMENTS

| | | | |
|---|---|---|---|
| EP | 0251304 | 1/1988 | |
| EP | 1662003 | 5/2006 | |
| EP | 2066336 | 9/2012 | |
| EP | 2537933 | 12/2012 | |
| KR | 10-2010-0019984 | * 9/2010 | ............... A61K 8/64 |
| WO | WO 1992012725 | 8/1992 | |
| WO | WO 1992012726 | 8/1992 | |
| WO | WO 199404180 | 3/1994 | |
| WO | WO 199417773 | 8/1994 | |
| WO | WO 1994022473 | 10/1994 | |
| WO | WO 199503411 | 2/1995 | |
| WO | WO 1995006058 | 3/1995 | |
| WO | WO 1995019780 | 7/1995 | |
| WO | WO 1996011953 | 4/1996 | |
| WO | WO 199634969 | 11/1996 | |
| WO | WO 1997003690 | 2/1997 | |
| WO | WO 1999032134 | 7/1999 | |
| WO | WO 199957297 | 11/1999 | |
| WO | WO 200022124 | 4/2000 | |
| WO | WO 200022137 | 4/2000 | |
| WO | WO 200029599 | 5/2000 | |
| WO | WO 200071718 | 11/2000 | |
| WO | WO 2001005821 | 1/2001 | |
| WO | WO 200117537 | 3/2001 | |
| WO | WO 200128569 | 4/2001 | |
| WO | WO 2001058950 | 8/2001 | |
| WO | WO 2002026265 | 4/2002 | |
| WO | WO 2002085300 | 10/2002 | |
| WO | WO 2004044006 | 5/2004 | |
| WO | WO 2004056850 | 7/2004 | |
| WO | WO 2004060300 | 7/2004 | |
| WO | WO 2004091517 | 10/2004 | |
| WO | WO 2004106486 | 12/2004 | |
| WO | WO 2004108088 | 12/2004 | |
| WO | WO 2005084712 | 9/2005 | |
| WO | WO 2006075138 | 7/2006 | |
| WO | WO 2006094530 | 9/2006 | |
| WO | WO 2006119170 | 11/2006 | |
| WO | WO 2006130580 | 12/2006 | |
| WO | WO 2008054585 | 5/2008 | |
| WO | WO 2009016043 | 2/2009 | |
| WO | WO 2009036568 | 3/2009 | |
| WO | WO 2010022227 | 2/2010 | |
| WO | WO 2010077853 | 7/2010 | |
| WO | WO 2011051489 | 5/2011 | |
| WO | WO 2011064399 | 6/2011 | |
| WO | WO 2011159878 | 12/2011 | |
| WO | WO 2012004384 | 1/2012 | |
| WO | WO 2012050923 | 4/2012 | |
| WO | WO 2013012414 | 1/2013 | |
| WO | WO 2013113008 | 8/2013 | |
| WO | WO 2013130913 | 9/2013 | |
| WO | WO 2014172392 | 10/2014 | |
| WO | WO 2014176373 | 10/2014 | |
| WO | WO 2014204816 | 12/2014 | |
| WO | WO 2015031316 | 3/2015 | |
| WO | WO 2015070060 | 5/2015 | |
| WO | WO 2015108785 | 7/2015 | |
| WO | WO 2015153753 | 10/2015 | |
| WO | WO 2015187295 | 12/2015 | |
| WO | WO 2016064817 | 4/2016 | |
| WO | WO 2016106229 | 6/2016 | |
| WO | WO 2016126615 | 8/2016 | |
| WO | WO 2016145388 | 9/2016 | |
| WO | WO 2016191587 | 12/2016 | |

OTHER PUBLICATIONS

Accession NP_036986.2; GI 148747382; Aug. 10, 2014.
Accession NP_776513.1; GI 41386772; Jan. 4, 2015.
Agata et al. (1996) "Expression of the PD-1 antigen on the surface of stimulated mouse T and B lymphocytes," *Int Immunol*; 8(5):765-772.
Aggen (2010) "Engineering Human Single-Chain T Cell Receptors," *Dissertation*; http://hdl.handle.net/2142/18585.
Alpdogan, et al., (2005) "IL-7 and IL-15: therapeutic cytokines for immunodeficiency", Cell, 26(1):56-64.

(56) References Cited

OTHER PUBLICATIONS

Alvarez et al. (2012) "Effects of PEGylation and Immune Complex Formation on the Pharmacokinetics and Biodistribution of Recombinant Interleukin10 in Mice," Drug Metab Dispos; 40(2):360-373.
Andre et al. (2004) "Oxaliplatin, Fluorouracil, and Leucovorinas Adjuvant Treatment for Colon Cancer," The New England Jounal of Medicine 350(23) 2343-2351.
Ansari and Raghava (2010) "Identification of conformational B-cell Epitopes in an antigen from its primary sequence," Immunome Res; 6:9pgs.
Ansell et al. (2002) "Phase 1 study of interleukin-12 in combination with rituximab in patients with B-cell non-Hodgkin lymphoma," Blood; 99:67-74.
Anstee and Goldin, (2006) "Mouse models in non-alcoholic fatty liver disease and steatohepatitis research", Int. J. Exp. Path., 87:1-16.
Arakawa and Tsumoto (2003) "The effects of arginine on refolding of aggregated proteins: not facilitate refolding, but suppress aggregation," Biochemical and Biophysical Research Communications; 304:148-152.
Armstrong et al. (1996) "Interleukin 10 (IL-10) regulation of tumour necrosis factor cx (TNF-cx) from human alveolar macrophages and peripheral blood monocytes," Thorax; 51:143-149.
Asadullah et al. (1999) "Interleukin 10 Treatment of Psoriasis," Arch Dermatol.; 135-187-192.
Asadullah et al. (2003) "Interleukin 10 Therapy—Review of a New Approach," Pharmacol, Rev.; 55-241-269.
Aukrust et al., (2005) "Potential role for immunomodulatory therapy in atherosclerotic plaque stabilization", Expert Opinion Pharmacother, 6:2169-2180.
Bajetta et al. (1998) "Pilot Study of Subcutaneous Recombinant Human Interleukin 12 in Metastatic Melanoma," Clinical Cancer Research; 4:75-85.
Banerjee et al. (2012) "Poly(ethylene glycol)-Prodrug Conjugates: Concept, Design, and Applications," Journal of Drug Delivery; Article ID 103973:17 pages.
Bea at al. (2011) "Performance Evaluation of a Multiplex Assay for Future Use in Biomarker Discovery Efforts to Predict Body Composition," Clin Chem Lab Med.; 49(5):817-824.
Berger et al. (2009) "Safety and immunologic effects of IL-15 administration in nonhuman primates," Blood; 114:2417-2426.
Berman et al. (1996) "Systemic administration of cellular IL-10 induces an effective, specific, and long-lived immune response against established tumors in mice," J Immunol; 157:231-238.
Bieghs, et al., (2012) "LDL Receptor Knock-Out Mice Are a Physiological Model Particularly Vulnerable to Study the Onset of Inflammation in Non-Alcoholic Fatty Liver Disease", PLoS ONE, 7(1):1-11.
Bilzer et al. (2006) "Role of Kupffer cells in host defense and liver disease," Liver International; 26:1175-1186.
BioLegend, "Recombinant Human IL-10 (carrier-free)", (2007) 3 pages.
Biswas et al. (2007) "Pathogen_specific CD8 T Cell Responses Are Directly Inhibited by IL-10," J Immunol.; 179:4520-4528.
Bork, Peer, (2000) "Powers and Pitfalls in Sequence Analysis: The 70% Hurdle", Genome Research, 10:398-400.
Bowie, James, U., et al. (1990) "Deciphering the Message in Protein Sequences: Tolerance to Amino Acid Substitutions", Science, 247:1306-1310.
Brady et al. (1994) "Reflections on a peptide," Nature; 368:692-693.
Brooks et al. (2008) "IL-10 and PD-L1 operate through distinct pathways to suppress T-cell activity during persistent viral infection," PNAS; 105(51):20428-20433.
Bruserud, O., et al., (1995) "Effects of interleukin 10 on blast cells derived from patients with acute myelogenous leukemia", Leukemia, 9:1910-1920.
Burgess (2009) "Refolding Solubilized Inclusion Body Proteins," Methods in Enzymology; 463:259-282.
Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.
Cai et al. (1999) "IL-10 enhances NK cell proliferation, cytotoxicity and production of IFN-q when combined with IL-18," Eur. J. Immunol.; 29:2658-2665.
Caliceti et al. (2012) "Effect of Plasma Membrane Cholesterol Depletion on Glucose Transport Regulation in Leukemia Cells," PLoS One; 7:e41246.
Cannistra & Niloff (1996) "Cancer of the uterine cervix," New Eng I J Med 334:1030-1038.
Cao et al. (2011) "Janus kinase activation by cytokine oncostatin M decreases PCSK9 expression in liver cells," J Lipid Res.; 52(3):513-530.
Capitini et al. (2009) "Modulating T cell Homeostasis with IL-7: Preclinical and Clinical Studies," J Intern Med; 266(2):141-153.
Cebon et al. (2003) "Two phase I studies of low dose recombinant human IL-12 with Melan-A and influenza peptides in subjects with advanced malignant melanoma," Cancer Immunity; 3:7 (18 pages).
Chamow et al. (1994) "Modification of CD4 Immunoadhesin with Monomethoxypoly(ethylene glycol) Aldehyde via Reductive Alkylation," Bioconjugate Chern.; 5:133-140.
Chan et al. (2015) "The Potentiation of IFN-γ and Induction of Cytotoxic Proteins by Pegylated IL-10 in Human CD8 T Cells," J Interferon Cytokine Res; 35(12):948-955.
Chang, et al., (2017) "CARs: Synthetic immunoreceptors for cancer therapy and beyond", Trends Mol. Med., 23:430-450.
Chen & Zlotnik (1991) "IL-10: A novel cytotoxic T cell differentiation factor," J Immunol; 147:528-534.
Chen et al. (2007) "Prediction of linear B-cell epitopes using amino acid pair antigenicity scale," Amino Acids; 33:423-428.
Cheon, H.G. (2013) "Latest research and development trends in non insulin antidiabetics", Arch. Pharm. Res., 36:145-153.
Chmielewski, et al, (2015) "TRUCKs: the fourth generation of CARs", Exp. Opin. Bioi. Ther., 15:1145-1154.
Choi et al, (2006) "Serum adiponectin, interleukin-10 levels and inflammatory markers in the metabolic 1-18 syndrome," Diabetes Research and Clinical Practice; 75:235-240.
Cindric, et al., (2007) "Structural 1-16 characterization of PEGylated rHuG-CSF and location of PEG attachment sites". Journal of Pharmaceutical and Biomedical Analysis. New York, NY. US, 44(2):388-395.
Collins et al. (2012) "Trastuzumab induces antibody-dependent cellmediated cytotoxicity (ADCC) in HER-2-non-amplified breast cancer cell lines," Annals of Oncology; 23:1788-1795.
Compton et al. (2004) "Pathogenesis of Enterotropic Mouse Hepatitis Virus in Immunocompetent and Immunodeficient Mice," Comparative Medicine; 54(6):681-689.
Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," Journal of Clinical Oncology; 33(1):74-82.
Cosma, Meda, (2014) :The impact of cytokines and chemokines on non-alcoholic fatty liver disease (NAFLD), Biotechnology, Molecular Biology and Nanomedicine, 2(1):15-16.
Couder et al. (1993) "Synthesis and biological activities of φ(CH2NH) pseudopeptide analogues of the C-terminal hexapeptide of neurotensin," Int. J. Peptide Protein Res.; 41:181-184.
D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," J. Exp. Med; 178:1041-1048.
Das et al. (2012) "IL-10-Producing Regulatory B Cells in the Pathogenesis of Chronic Hepatitis B Virus Infection," J. Immunol.; 189(8):3925-3935.
Davidson & Diamond (2001) "Autoimmune diseases," New Engl J Med; 345:340-350.
De Waal Malefyt et al. (1991) "Interleukin 10 (IL-10) and viral IL-10 strongly reduce antigen-specific human T cell proliferation by diminishing the antigen-presenting capacity of monocytes via

(56) References Cited

OTHER PUBLICATIONS downregulation of class II major histocompatibility complex expression," *J Exp Med*; 174(4):915-924.
De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.
Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.
Dinant, et al., (2007) "IL-10 attenuates hepatic I/R injury and promotes hepatocyte proliferation", J. Surg. Res., 141:176-182.
Dolgin (2011) "Trial puts niacin—and cholesterol dogma—in the line of fire," *Natue Medicine*; 17(7):356.
Dorner et al. (2011) "A genetically humanized mouse model for hepatitis C virus infection," *Nature*; 474:208-211.
Easy Surf. Blood Volume Calculator [online]Oct. 1, 2012 [retrieved Aug. 18, 2014]. Available on the internet: <URL:https://web.archive.org/web/20121001142649/http://www.easysurf.cc/cnver22.htm >.
Ehrilich et al. (2013) "Preparation and Characterization of Albumin Conjugates of a Truncated Peptide YY Analogue for Half-Life Extension," *Bioconjug. Chem.*; 24(12):2015-2024.
El-Manzalawy et al. (2008) "Predicting linear B-cell epitopes using string kernels," *J Mol Recognit*; 21:243-255.
Emmerich et al. (2012) "IL-10 directly activates and expands tumor-resident CD8(+) T cells without de novo infiltration from secondary lymphoid organs," *Cancer Res*; 72(14):3570-3581.
Emmerich J., et al., (2012) "Autochthonous T cells to the rescue: IL-10 directly activates tumor-resident CD8(+) T cells", Oncoimmunology, 1(9):1637-1639.
Engel et al. (2006) "Using Endoproteinases Asp-N And Glu-C to Improve Protein Characterization," *Promega Corporation*; 10th edition.
Enzinger & Mayer (2003) "Esophageal cancer," *New Eng I J Med*; 349:2241-2252.
Fahnert et al. (2012) "Using Folding Promoting Agents in Recombinant Protein Production: A Review," *Methods inn Molecular Biology*; 824:3-36.
Fang et al. (2015) "Programmed Death 1 (PD-1) is involved in the development of proliferative diabetic retinopathy by mediating activation-induced apoptosis," *Mol Vis*; 21:901-910.
Farrar et al. (1999) "Cancer dormancy. VII. A regulatory role for COB+ T cells and IFN-gamma in establishing and maintaining the tumor-dormant state," *J Imunol* 162:2842-2849.
FDA: Limit Use of 80 mg Simvastatin, Jun. 8, 2011, (https://www.fda.gov/ForConsumers/ConsumerUpdates/ucm257884.htm) 3 pages.
Fehniger and Caligiuri (2001) "Interleukin 15: biology and relevance to human disease," *Blood*; 97:14-32.
Feingold et al. (1996) "Endotoxin, TNF, and IL-I decrease cholesterol 7a-hydroxylase mRNA levels and activity," *Journ of Lipid Res*; 37:223-228.
Fichtlscherer et al., (2004) "Interleukin-10 serum levels and systemic endothelial vasoreactivity in patients with coronary artery desease", J. Am. Coll. Cardiol., 44:44-49.
Fiorentino et al. (1989) "Two types of mouse T helper cell. IV. Th2 clones secrete a factor that inhibits cytokine production by Th1 clones," *J Exp Med*; 170:2081-2095.
Forastiere et al. (2001) "Head and neck cancer," *New Engl J Med* 345:1890-1900.
Fridman et al. (2012) "The immune contexture in human tumours: impact on clinical outcome," *Nature*; 12:298-306.
Fry and Mackall (2002) "Interleukin-7: from bench to clinic," *Blood*; 99:3892-3904.
Fry and Mackall (2005) "The Many Faces of IL-7: From Lymphopoiesis to Peripheral T Cell Maintenance", the Journal of Immunology, 174:6571-6576.
Fujiwara et al. (2010) "Extraction and purification of human interleukin-10 from transgenic rice seeds," *Protein Expression and Purification*; 72:125-130.

Galon et al. (2013) "The Continuum of Cancer Immunosurveillance: Prognostic, Predictive, and Mechanistic Signatures," *Immunity*; 39:11-26.
Gameren et al. (1994) "Effects of Recombinant human interleukin-6 in cancer patients: a phase I-II study," Blood; 84:1434-1441.
Gao et al. (2012) "BEST: Improved Prediction of B-Cell Epitopes from Antigen Sequences," *PLoS ONE*; 7(6): e40104.
Gargett et al.: 11 Different cytokine and stimul ation conditions influence t he expansion and immune phenotype of third-generat ion chimeric antigen receptor T cells specific for tumor antigen GD2, Cytotherapy, vol. 17 , No. 4, Apr. 2015 (Apr. 2015) , pp. 487-495.
GenBank Accession No. M37897 "Mouse interleukin 10 mRNA, complete cds," dated Apr. 27, 1993.
GenBank Accession No. NP 000563 "interleukin-10 precursor [*Homo sapiens*]," dated Mar. 3, 1995.
Georgescu et al. (1997) "Interleukin-10 Promotes Activation-induced Cell Death of SLE Lymphocytes Mediated by Fas Ligand," *J. Clin. Invest.*; 100:2622-2633.
Gerstein et al. (2008) "Effects of Intensive Glucose Lowering in Type 2 Diabetes," *New England J of Medicine*; 358(24):2545-2559.
Gesser et al. (1997) "Identification of functional domains on human interleukin 10," *Proc. Natl. Acad. Sci.*; 94:14620-14625.
Gierens et al. (2000) "Interleukin-6 Stimulates LDL Receptor Gene Expression via Activation of Sterol-Responsive and Sp1 Binding Elements," *Arterioscler Thromb Vasc Biol.*; 20:1777-1783.
Gill et al., (2015) "Going viral: Chimericantigen receptor T-cell therapy forhematological malignancies", Immunological Reviews 28150181 Blackwell Publishing Ltd GBR, 263(1):68-89.
Gosh et al. (2007) "FOLFOX-6 Combination as the First-Line Treatment of Locally Advanced and/or Metastatic Pancreatic Cancer," American Journal of Clinical Oncology 30(1) 15-20.
Gotoh, et al., (2012) "A novel anti-inflammatory role for spleen-derived Interleukin-10 in obesity-induced inflammation in white adipose tissue and liver", Diabetes, 61:1994-2003.
Gotoh, Kora, et al., (2017) "Role of spleen-derived IL-10 in prevention of systemic low-grade inflammation by obesity", Endocrine Journal, 64(4):375-378.
Gregoriadis et al., (2005) "Improving the therapeutic efficacy of peptides and proteins: a role for polysialic acids," *Int. J. Pharmaceutics*; 300(1-2):125-130.
Groux et al. (1998) "A transgenic model to analyze the immunoregulatory role of IL-10 secreted by antigen-presenting cells," *J Immunol*; 162:1723-1729.
Groux et al. (1998) "Inhibitory and stimulatory effects of IL-10 on human COB+ T cells," *J Immunol*; 160:3188-3193.
Hagenbaugh et al. (1997) "Altered immune responses in interleukin 10 transgenic mice," *J Exp Med*; 185:2101-2110.
Hamada et al. (2009) "Effect of Additives on Protein Aggregation," *Current Pharm Biotech*; 10:400-407.
Hashizume et al. (2010) "Overproduced interleukin 6 decreases blood lipid levels via upregulation of very-low-density lipoprotein receptor," *Ann Rheum Dis*; 69:741-746.
Heeschen et al. (2003) "Serum Level of the Antiinflammatory Cytokine Interleukin-1 0 Is an Important Prognostic Determinant in Patients With Acute Coronary Syndromes," *Circulation*; 107:2109-2114.
Hermanson, et al., (2015) "Utilizing chimeric antigen receptors to direct natural killer cell activity", Frontiers in Immunology, 6:195.
Hombach et al. (2013) "Arming Cytokine-induced Killer Cells With Chimeric Antigen Receptors: CD28 Outperforms Combined CD28-0X40 'Super-stimulation'," *Molecular Therapy*; 12:2268-2277.
Hombach, et al., (2012) "OX40 costimulation by a chimeric antigen receptor abrogates CD28 and IL-2 induced IL-10 secretion by redirected CD4+ T cells", Oncolmmunol., 1:458-466.
Howard et al. (1993) "Interleukin 10 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.
Huang et al. (2010) "Depletion of Liver Kupffer Cells Prevents the Development of Diet-Induced Hepatic Steatosis and Insulin Resistance," 59:347-357.

(56) References Cited

OTHER PUBLICATIONS

Huntington et al. (2008) "IL-15 trans-presentation promotes human NK cell development and differentiation in vivo," *J. Exp. Med.*; 206:25-34.
Hustoft et al. (2012) "A Critical Review of Trypsin Digestion for LC-MS Based Proteomics," *InTech*; Chapter 4.
Infante et al. (2015) "A first-in-human dose escalation study of PEGylated recombinant human IL-10 (AM0010) in advanced solid tumors," *ASCO Meeting Abstracts*; 33(15 suppl):3017.
International Search Report PCT/US01/42431, dated Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.
Izbicki et al. (1997) "Prognostic value of immunohistochemically identifiable tumor cells in lymph nodes of patients with completely resected esophageal cancer," *New Engl J Med*; 337:1188-1194.
Jameson et al. (1994) "A rationally designed CD4 analogue inhibits experimental allergic encephalomyelitis," *Nature*; 368:744-746.
Jaspers, et al., (2017) "Development of Cart cells designed to improve antitumor efficacy and safety", Pharmac. & Therap., http://dx.doi.org,/1 0.1016/j.pharmthera.2017.03.012.
Jensen, et al., (2015) "Designing chimeric antigen receptors to effectively and safely target tumors", Curr. Opin. Immunol., 33:9-15.
Jevševar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure Of The IL-10/1L-10R1 Complex Reveals A Shared Receptor Binding Site," *Immunity*; 14:35-46.
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.
Khow and Suntrarachun (2012) "Strategies for production of active eukaryotic proteins in bacterial expression system," *Asian Pac, J. Biomed.*; 2(2):159-162.
Kimball et al (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.
Kinstler et al. (1996) "Characterization and Stability of N-terminally PEGylated rhG-CSF," *Pharm. Res.*; 13:996-1002.
Kinstler et al. (2002) "Mono-N-terminal poly(ethylene glycol)—protein conjugates," *Advanced Drug Delivery Reviews*; 54:477-485.
Klebanoff, CA et al., (2004) "IL-15 Enhances the in vivo Antitumor Activity of Tumor-reactive CD8+ T Cells", Proceedings of the National Academy of the Sciences of the U.S.A., 101(7)1 969-1974.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.
Kokura et al. (2003) "The blocking of NFkB activation by systemicinterleukin-10 gene therapy inhibits liver and lung metastasis of colon 26 adenocarcinoma in mice" *Gastroenterology*; 124(4): Abstract No. W965.
Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin M in the regulation of plasma lipid levels," *Journal of Lipid Research*; 46:1163-1171.
Körholz et al. (1997) "The Role of Interleukin-10 (IL-10) in IL-15-Mediated T-Cell Responses," *Blood*; 90(11):4513-4521.
Kumagai, et al., (2013) "Effects of Ezetimibe on hypercholesterolemia in the lipid profile in patients with metabolic syndrome", IJC Metabolic and Endocrine, 1:7-12.
Kundu et al. (1996) "Antimetastatic and antitumor activities of interleukin 10 in a murine model of breast cancer," *J Nail Cancer Inst*; 88:536-541.
Kundu et al. (1997) "Interleukin-10 inhibits tumor metastasis, down regulates MHC class I, enhances NK lysis," *Cellular Immunology, Academic Press*; 180(1):55-61.
Kute et al. (2012) "Understanding key assay parameters that affect measurements of trastuzumab-mediated ADCC against Her2 positive breast cancer cells," *OncoImmunology*; 1(6):810-821.
Langowski et al. (2006) "IL-23 promotes tumour incidence and growth," *Nature*; 442:461-465.
Larter and Yeh, (2008) "Animal models of NASH: Getting both pathology and metabolic context right", Journal of Gastroenterology and Hepatology, 23:1635-1648.
Lasek et al. (2014) "Interleukin 12: still a promising candidate for tumor immunotherapy?" *Cancer Immunol Immunother*; 63:419-435.
Lauw, Fanny, et al., (2000) "Proinflammatory Effects of IL-10 During Human Endotoxemia", J Immunol, 165:2783-2789.
Lazar, Eliane, et al. (1988) "Transforming Growth Factor alpha: Mutation of Aspartic Acid 47 and Leucine 48 Results in Different Biological Activities", Mol. Cell. Bioi., 8:12471252.
Le et al. (2001) "Pre-existing tumor-sensitized T cells are essential for eradication of established tumors by IL-12 and cyclophosphamide plus IL-12," *J Immunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pp.).
Lewington and Clark (2005) "Combined Effects of Systolic Blood Pressure and Total Cholesterol on Cardiovascular Disease Risk," *Circulation*; 112:3373-3374.
Liang, et al., (2014) "Establishment of a General NAFLD Scoring System for Rodent Models and Comparison to Human Liver Pathology", PLOSone, 17 pages.
Liedtke, et al., (2013) "Experimental liver fibrosis research: update on animal models, legalissues and translational aspects", Fibrogenesis Tissue Repair, 6(19):1-25.
Lindhout et al. (2011) "Site-specific enzymatic polysialylation of therapeutic proteins using bacterial enzymes," *PNAS*; 108(18)7397-7402.
Lindsay et al., (2002) "IL-10 gene therapy prevents TNBS-induced colitis," Gene Therapy, 9(24):1715-1721.
Liu et al. (2003) "IL-10 Mediates Suppression of the CD8 T Cell IFN-γ Response to a Novel Viral Epitope in a Primed Host," *J Immunol*; 171:4765-4772.
Loebbermann et al. (2012) "IL-10 Regulates Viral Lung Immunopathology during Acute Respiratory Syncytial Virus Infection in Mice," *PLoS ONE*; 7(2):e32371.
Lopez et al. (2005) "IL-12 and IL-10 Expression Synergize to Induce the Immune-Mediated Eradication of Established Colon and Mammary Tumors and Lung Metastasis," *J Immunol*; 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.
Lugli et al. (2010) "Transient and persistent effects of IL-15 on lymphocyte homeostasis in nonhuman primates," *Blood*; 116:3238-3248.
Lynch and Chapelle (2003) "Hereditary colorectal cancer," New Eng I J Med; 348:919-932.
Martin et al. (2001) "B-Cell Deficiency Suppresses Vaccine-Induced Protection against Murine Filariasis but Does Not Increase the Recovery Rate for Primary Infection," *Infect. Immun.*; 69(11):7067-7073.

(56) References Cited

OTHER PUBLICATIONS

Mattos et al. (2012) "PEGylation of interleukin-10 improves the pharmacokinetic profile and enhances the antifibrotic effectivity in CCl.-induced fibrogenesis in mice," *J Control Release*; 162(1):84-91.
Maus et al. (2014) "Antibody-modified T cells: CARs take the front seat for hematologic malignancies," *Blood*; 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.
Millic, Sandra, et al., (2014) "Non-alcoholic fatty liver disease and obesity: Biochemical, metabolic and clinical presentations", World J Gastroenterol, 20(28):9330-9337.
Monk (2011) "A Strategy for the Quantification of Protein Polyethylene Glycol (PEG) Derivatized Sites using iTRAQ," *University of California*, San Diego; 1-51.
Moore et al. (1990) "Homology of cytokine synthesis inhibitory factor (IL-10) to the Epstein-Barr virus gene BCRFI," *Science*; 248:1230-1234.
Moran et al. (1994) "Human leukemia inhibitory factor inhibits development of experimental atherosclerosis," *Arterioscler Thromb Vasc Biol.*; 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.
Muecke, Susanne, et al., (2000) "Suppression of the Tumorigenic Growth of Burkitt's Lymphoma Cells in Immunodeficient Mice by Cytokine Gene Transfer Using Ebv-Derived Episomal Expression Vectors", Int. J. Cancer, 86:301-306.
Mumm et al. (2011) "IL-10 elicits IFNγ-dependent tumor immune surveillance," *Cancer Cell*; 20(6):781-796.
Mumm et al., (2013) "Pegylated .IL-10 induces cancer immunity the surprising role of IL-10 as a potent inducer of IFN-g-mediated C_D8p T cell cytotoxicity," BioEssays, 35:623-631.
Mumm, Jb and Oft M., (2008) "Cytokine-based transformation of immune surveillance into tumor-promoting inflammation", Oncogene, 27(45):5913-5919.
Mumm, John B., et al., (2012) "Killing from within", Oncoimmunology, 1(9):1598-1600.
Naicker et al. (2009) "Interleukin-10 Promoter Polymorphisms Influence HIV-1 Susceptibility and Primary HIV-1 Pathogenesis," *J. Infect. Dis.*; 200(3):448-452.
Natsume et al. (2009) "Improving effector functions of antibodies for cancer treatment: Enhancing ADCC and CDC," *Drug Design, Development and Therapy*; 3:7-16.
NCT01025297, (2012) ""Dose Escalation Study of Interleukin7(IL7) and Bitherapy in HCV Genotype 1 or 4 Patients Resistant to Bitherapy Alone (Eclipse 2)"", Clinical Trials, 6 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Dec. 11, 2013, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 31, 2014, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jul. 17, 2014, 6 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.
NCT02923921, "Randomized Study of AM0010 in Combination With Folfox Compared to FOLFOX Alone as Secondline Tx in Pts With Meta Pancreatic Cancer That Has Progressed During or Following a FirstLine Gemcitabine Containing Regimen", ClinicalTrials.gov, Oct. 4, 2016, 3 pages.
Nelson, David R., (2003) "Long-Term Interleukin 10 Therapy in Chronic Hepatitis C Patients Has a Proviral and Anti-inflammatory Effect", Hepatology, 38(4):859-868.
Nenseter et al. (1992) "Role of liver endothelial and Kupffer cells in clearing low density lipoprotein from blood in hypercholesterolemic rabbits," *J of Lipid Res*; 33:867-877.
Neven et al. (2013) "A Mendelian predisposition to B cell lymphoma caused by IL-10R deficiency," *Blood*; 122(23):3712-3722.
Newick, et al., (2016) "Cart cell therapy for solid tumors", Annu. Rev. Med., 68:139-152.
Neyrinck et al. (2009) "Critical role of Kupffer cells in the management of diet-induced diabetes and obesity," *Biochemical and Biophysical Research Communications*; 385:351-356.
Neyrinck, Audrey, et al., (2002) "Inhibition of Kupffer cell activity induces hepatic triglyceride synthesis in fasted rats, independent of lipopolysaccharide challenge", Journal of Hepatology, 36:466-473.
Nicholls et al. (2012) "Is niacin ineffective? or did AIM-HIGH miss its target?," *Cleveland Clinic Journ of Med*; 79(1):38-43.
Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.
Osaki et al. (1999) "Potent antitumor effects mediated by local expression of the mature form of the interferon-γ inducing factor, interleukin-18 (IL-18)," *Gene Therapy*; 6:808-815.
Osborne (1998) "Tamoxifen in the treatment of breast cancer," *New Engl J Med*; 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology*; 187:3383-3390.
Pardoll (2012) "The blockade of immune checkpoints in cancer immunotherapy," *Cancer*; 12:252-264.
Park et al. (2011) "IL-15-Induced IL-10 Increases the Cytolytic Activity of Human Natural Killer Cells," *Mol. Cells*; 32:265-272.
Pasut and Veronese (2012) "State of the art in PEGylation: the great versatility achieved after forty years of research," *Journal of Controlled Release*; 161:461-472.
Paulsen and Reichelt, (1992) "Mouse liver regeneration after carbon tetrachloride injury as test system for hepatic growth regulators" Virchovvs Archiv B Cell Pathol, 62:173-177.
Payne et al. (2010) "Product development issues for PEGylated proteins," *Pharmaceutical Development and Technology*; 16:423-440.
Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.
Pellegrini et al. (2011) "IL-7 Engages Multiple Mechanisms to Overcome Chronic Viral Infection and Limit Organ Pathology," *Cell*; 144:1-13.
PeproTech, "Recombinant Human IL-10 (carrier-free)", (2017) 7 pages.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.

(56) References Cited

OTHER PUBLICATIONS

Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.
Rachmawati et al. (2007) "Chemical Modification of Interleukin-10 with Mannose 6-Phosphate Groups Yields a Liver-Selective Cytokine," *Drug Metabolism and Disposition*; 35(5):814-821.
Radwanski et al. (1998) "Pharmacokinetics and Leukocyte Responses of Recombinant Human Interleukin-10," *Pharm. Res.*; 15(12):1895-1901.
Ramirez-Montagut et al. (2003) "Immunity to melanoma: unraveling the relation of tumor immunity and autoimmunity," *Oncogene*; 22:3180-3187.
Re et al. (2002) "Preclinical evaluation of the antiproliferative potential of ST1571 in Hodgkin's disease," *British Journal of Cancer*; 86:1333-1335.
Recombinant Human IL-1 0 Protein, CF R&D Systems, accessed Feb. 22, 2016.
Reynolds, et al. (2002) "Proteolytic 18O Labeling for Comparative Proteomics: Evaluation of Endoprotease Glu-C as the Catalytic Agent," *Journal of Proteorne Research*; 1(1):27-33.
Roberts et al. (2012) "Chemistry for peptide and protein PEGylation," *Advanced Drug Delivery Reviews*; 64:116-127.
Rolfe et al. (2003) "Leukaemia inhibitory factor retards the progression of atherosclerosis," *Cardiovascular Research*; 58:222-230.
Russo et al. (2006) "Randomized trial of pegylated interferon a-2b monotherapy in haemodialysis patients with chronic hepatitis C," *Nephrol Dial Transplant*; 21:437-443.
Saha and Raghava (2006) "Prediction of continuous B-cell epitopes in an antigen using recurrent neural network," *Proteins*; 65:40-48.
Sakamoto et al. (2003) "Interleukin-10 gene therapy enhances antitumor effect of CPT-11 for lung metastasis of colon26 adenocarcinoma in mice," *Gastroenterology*; 124(4):A456-A457.
Sawaya et al. (2003) "Risk of cervical cancer associated with extending the interval between cervical-cancer screenings," *New Engl J Med*; 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.
Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.
Scotton and Chambers, (2010) "Bleomycin revisited: towards a more representative model of IPF?", Am J Physiol Lung Cell Mol Physiol, 299:L439-L441.
Sela and Zisman (1997) "Different roles of D-amino acids in immune phenomena," Faseb J.; 11:449-456.
Shen et al. (2013) "Proprotein convertase subtilisin/kexin type 9 potentially influences cholesterol uptake in macrophages and reverse cholesterol transport," FEBS Letters; 587:1271-1274.
Sinha, Ian, et al. "A Systematic Review of Studies That Aim to Determine Which Outcomes to Measure in Clinical Trials in Children", PLOS:One, Apr. 29, 2008, 13 pages.
Smith et al. (1996) "Administration of interleukin-1 0 at the time of priming protects Corynebacterium parvum-primed mice against LPS- and TNF-alpha-induced lethality," *Cellular Immunology* 173(2):207-214.
Sneller et al. (2011) "IL-15 administered by continuous infusion to rhesus macaques induces massive expansion of CD8 T effector memory population in peripheral blood," *Blood*; 118(26):6845-6848.
Soderquist, et al. (2010) "PEGylation of interleukin-1 0 for the mitigation of enhanced pain states", J Biomed Mater Res A, 3(93):1169-1179.

Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.
Song et al. (2012) "CD27 costimulation augments the survival and antitumor activity of redirected human T cells in vivo," *Blood*; 119(3):696-706.
Spoto, et al., (2013) "Spleen IL-10, A Key Player in Obesity-Driven Renal Risk", Nephrol Dial Transplant, 28:1061-1064.
Srivastava et al. (2013) "Effects of interleukin-18 on natural killer cells: costimulation of activation through Fc receptors for immunoglobulin," *Cancer Immunol Immunother*; 62(6):1073-1082.
Steel, JC et al., (2012) "Biology and its Therapeutic Implications in Cancer", Trends in Pharmacological Sciences, 33(1):35-41.
Stoklasek, et al., (2006) "Combined IL-15/IL-15Rα Immunotherapy Maximizes IL-15 Activity In Vivo", J Immunol, 177(9):6072-6080.
Storek, et al., (2003) ""Interleukin-7 improves CD4 T-cell reconstitution after autologous CD34 celltransplantation in monkeys"", Blood, 101(10):4209-4218.
Storici and Resnick (2006) "The delitto perfetto approach to in vivo site-directed mutagenesis and chromosome rearrangements with synthetic oligonucleotides in yeast," *Methods in Enzymology*; 409:329-345.
Sweredoski and Baldi (2009) "COBEpro: a novel system for predicting continuous B-cell epitopes," *Protein Eng Des Sel*; 22:113-120.
Syto et al. (1998) "Structural and biological stability of the human interleukin 10 homodimer," *Biochemistry*; 37(48):16943-16951.
Teng et al. (2015) "IL-12 and IL-23 cytokines: from discovery to targeted therapies for immune-mediated inflammatory diseases," *Nature Medicine*; 21:719-729.
Teng et al., (2011) "Stable IL-10: A new therapeutic that promotes tumor immunity" Cancer Cell 2011 Cell Press USA, 20(6):691-693.
Tilg et al. (2002) "Treatment of Crohn's disease with recombinant human interleukin 10 induces the proinflammatory cytokine interferon γ," *Gut*; 50:191-195.
Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.
Tréhin et al. (2004) "Cellular uptake but low permeation of human calcitonin-derived cell penetrating peptides and Tat(47-57) through well-differentiated epithelial models," *Pharm. Research*; 21:1248-1256.
Tsumoto et al. (2003) "Practical considerations in refolding proteins from inclusion bodies," *Protein Expression and Purification*; 28:1-8.
Tsumoto et al. (2004) "Role of Arginine in Protein Refolding, Solubilization, and Purification," *Biotechnol. Prog.*; 20:1301-1308.
UniProt reference A2T6Z6 (1L 1 O_PANTR) (downloaded from http://www.uniprot.org/uniprot!A2T6Z6, last sequence update Mar. 6, 2007).
UniProt reference P79338 (1L 1 O_MACFA) (downloaded from http://www.uniprot.org/uniprot/P79338, last sequence update May 1, 1997).
Valabrega et al. (2007) "Trastuzumab: mechanism of action, resistance and future perspectives in HER2-overexpressing breast cancer," *Annals of Oncology*; 18:977-984.
Van Deventer et al. (1997) "Multiple Doses of Intravenous Interleukin 10 in Steroid-Refractory Crohn's Disease," *Gastroenterology*, 113:383-389.
Vicari and Trinchieri (2004) "Interleukin-10 in viral diseases and cancer: exiting the labyrinth?," *Immunological Reviews*; 202:223-236.
Vigneron et al. (2013) "Database of T cell-defined human tumor antigens: the 2013 update," *Cancer Immunity*; 13:15-20.
Virgin, et al. (2009) "Redefining Chronic Viral Infection," *Cell*; 138:30-50.
Von Andrian and Mackay (2000) "T-cell function and migration. Two sides of the same coin," *New Engl J Med*; 343:1020-1034.
Waldmann et al. (2011) "Safety (toxicity), pharmacokinetics, immunogenicity, and impact on elements of the normal immune system of recombinant human IL-15 in rhesus macaques," *Blood*; 117:4787-4795.

(56) References Cited

OTHER PUBLICATIONS

Walter and Nagabhushan (1995) "Crystal structure of interleukin 10 reveals an interferon gamma-like fold," *Biochemistry*; (38):12118-12125.
Wan, Jinghong, et al., (2014) "M2 Kupffer Cells Promote M1 Kupffer Cell Apoptosis: A Protective Mechanism Against Alcoholic and Nonalcoholic Fatty Liver Disease", Hepatology, 59(1):131-142.
Wee et al. (2010) "SVM-based prediction of linear B-cell epitopes using Bayes Feature Extraction," *BMC Genomics*; 11(Supp 4):521.
Wender et al. (2000) "The design, synthesis, and evaluation of molecules that enable or enhance cellular uptake: peptoid molecular transporters," *Proc. Natl. Acad. Sci. USA*; 97:13003-13008.
Wilson et al. (2011) "The role of IL-10 in regulating immunity to persistent viral infections," *Curr Top Microbiol Immunol.*; 350: 39-65.
Witsch et al. (2010) "Roles for Growth Facotes in Cancer Progression," *Physiology*; 25(2):85-101.
Woodhouse, Stephen D., et al., (2010) "Transcriptome Sequencing, Microarray, and Proteomic Analyses Reveal Cellular and Metabolic Impact of Hepatitis C Virus Infection InVitro", Hepatology, 52(2):443-453.
Wu et al. (2012) "Immunotherapies: The Blockade of Inhibitory Signals," *Int. J. Biol. Sci.*: 8:1420-1430.
Wylie, Davic, C., et al.; (2001) "Carboxyalkylated Histidine Is a pH-Dependent Product of Pegylation with SC-PEG", Pharmaceutical Research, 18(9):2-8.

Xu et al. (2010) "Regulation of Antitumor Immune Responses by the IL-12 Family Cytokines, IL-12, IL-23, and IL-27," *Clinical and Developmental Immunology*; Article ID:832454 (9 pages).
Yamaguchi and Miyazaki (2014) "Refolding Techniques for Recovering Biologically Active Recombinant Proteins from Inclusion Bodies," *Biomolecules*; 4:235-251.
Yoshioka et al. (2011) "Development of a novel DDS for site-specific PEGylated proteins," *Chem. Central J.*; 5:25.
Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.
Zauner et al. (1996) "Glycerol Enhancement of Ligand-Polylysine/DNA Transfection," *Bio Techniques*; 20:905-913.
Zdanov et al. (1995) "Crystal structure of interleukin-10 reveals the functional dimer with an unexpected topological similarity to interferon γ," *Structure*; 3:591-601.
Zdanov et al. (1996) "Crystal structure of human interleukin-10 at 1.6 A resolution and a model of a complex with its soluble receptor," *Protein Sci.*; (10):1955-1962.
Zender et al. (2002) "VP22-mediated intercellular transport of p53 in hepatoma cells in vitro and in vivo," *Cancer Gene Ther.*; 9(6):489-496.
Zheng et al. (1996) "Interleukin-10 inhibits tumor metastasis through an NK cell-dependent mechanism," *J Exp Med*; 184:579-584.

\* cited by examiner

Fig. 1A. IL-15 Long Signal Peptide (LSP) Protein (accession no. BC018149.2) (SEQ ID NO:1)

MRISKPHLRSISIQCYLCLLLNSHFLTEAGIHVFILGCFSAGLPKTEANWVNVISDLKKIEDLIQSMHI
DATLYTESDVHPSCKVTAMKCFLLELQVISLESGDASIHDTVENLIILANNSLSSNGNVTESGCKEC
EELEEKNIKEFLQSFVHIVQMFINTS

Fig. 1B. IL-15 Short Signal peptide (SSP) Protein (accession no. BC100962.1) (SEQ ID NO:2)

MVLGTIDLCSCFSAGLPKTEANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQMFINTS

Fig. 1C. Mature human IL-15 Protein (SEQ ID NO:3)

NWVNVISDLKKIEDLIQSMHIDATLYTESDVHPSCKVTAMKCFLLELQVISLESGDASIHDTVENLII
LANNSLSSNGNVTESGCKECEELEEKNIKEFLQSFVHIVQMFINTS

Fig. 2A.   Long Signal Peptide (LSP) cDNA Open Reading Frame (ORF) (accession no. BC018149.2) (SEQ ID NO:4)

atgagaatttcgaaaccacatttgagaagtatttccatccagtgctacttgtgtttacttctaaacagtcattttctaactgaagctggcattcatgtcttcattttggg
ctgtttcagtgcagggcttcctaaaacagaagccaactgggtgaatgtaataagtgatttgaaaaaaattgaagatcttattcaatctatgcatattgatgctactt
tatatacggaaagtgatgttcaccccagttgcaaagtaacagcaatgaagtgctttctcttggagttacaagttatttcacttgagtccggagatgcaagtattca
tgatacagtagaaaatctgatcatcctagcaaacaacagtttgtcttctaatgggaatgtaacagaatctggatgcaaagaatgtgaggaactggaggaaaaa
aatattaaagaattttttgcagagttttgtacatattgtccaaatgttcatcaacacttcttga Fig. 2B.   Short Signal peptide (SSP) cDNA Open Reading Frame (ORF) (accession no. BC100962.1) (SEQ ID NO:5)

atggtattgggaaccatagatttgtgcagctgtttcagtgcagggcttcctaaaacagaagccaactgggtgaatgtaataagtgatttgaaaaa
aattgaagatcttattcaatctatgcatattgatgctactttatatacggaaagtgatgttcaccccagttgcaaagtaacagcaatgaagtgctttct
cttggagttacaagttatttcacttgagtccggagatgcaagtattcatgatacagtagaaaatctgatcatcctagcaaacaacagtttgtcttcta
atgggaatgtaacagaatctggatgcaaagaatgtgaggaactggaggaaaaaaatattaaagaattttttgcagagttttgtacatattgtccaaa
tgttcatcaacacttcttga Fig. 2C.   Nucleic acid sequence encoding Mature Human IL-15 Protein (SEQ ID NO:6)

aactgggtgaatgtaataagtgatttgaaaaaaattgaagatcttattcaatctatgcatattgatgctactttatatacggaaagtgatgttcaccccagttgcaa
agtaacagcaatgaagtgctttctcttggagttacaagttatttcacttgagtccggagatgcaagtattcatgatacagtagaaaatctgatcatcctagcaaac
aacagtttgtcttctaatgggaatgtaacagaatctggatgcaaagaatgtgaggaactggaggaaaaaaatattaaagaattttttgcagagttttgtacatattg
tccaaatgttcatcaacacttcttga

METHODS OF USING COMBINATIONS OF PEG-IL-10 AND IL-15 FOR TREATING CANCERS

CROSS-REFERENCE TO RELATED APPLICATION

The present application claims priority benefit of U.S. provisional application Ser. No. 62/209,500, filed Aug. 25, 2015, which application is incorporated herein by reference in its entirety.

FIELD OF THE INVENTION

This invention relates to methods of using a PEG-IL-10 in combination with other agents in the treatment or prevention of a diverse array of diseases and disorders, including cancers and immune-related disorders.

INTRODUCTION

The cytokine interleukin-10 (IL-10) is a pleiotropic cytokine that regulates multiple immune responses through actions on T cells, B cells, macrophages, and antigen presenting cells (APC). IL-10 can suppress immune responses by inhibiting expression of IL-1α, IL-1β, IL-6, IL-8, TNFα, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601).

As a result of its pleiotropic activity, IL-10 has been linked to a broad range of diseases, disorders and conditions, including inflammatory conditions, immune-related disorders, fibrotic disorders, metabolic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

SUMMARY

The present disclosure contemplates methods of using a PEG-IL-10 (e.g., rHuPEG-IL-10), and compositions thereof, in combination with an IL-15 agent (e.g., rHuIL-15), and compositions thereof, for the treatment and/or prevention of cancer-related diseases, disorders and conditions, and/or the symptoms thereof. The methods comprise particular dosing regimens and provide the opportunity for additive or synergistic effects in the treatment and/or prevention of the cancer-related diseases, disorders and conditions described herein. Moreover, such combination therapy often allows for reductions in the amounts and/or frequencies of administration of the PEG-IL-10 and/or the IL-15 agent in which it is combined, which can result in any adverse effects being minimized or obviated. The combination therapy encompasses co-administration when the PEG-IL-10 and IL-15 agent are administered separately (e.g., two distinct pharmaceutical compositions) or together (e.g., one pharmaceutical composition comprising both the PEG-IL-10 and the IL-15 agent).

IL-10 is deemed to be an anti-inflammatory and immunosuppressive cytokine that inhibits the secretion of IFNγ, IL-12 and TNFα. It also inhibits antigen presentation and subsequent activation of CD4+ T cells and is thus widely considered to be a potent immune suppressive cytokine. In contrast, IL-15 is a pro-inflammatory cytokine involved in the stimulation of cytolytic activity, cytokine secretion, and survival of NK cells, CD8+ memory T-cells and naïve CD8+ cells. IL-15 induces the proliferation of naïve and memory CD4 and CD8+ T cells and NK cells, induces the secretion of IFNγ, TNFα, IL-10 and IL-6, and enhances the cytotoxic function of both CD8+ T cells and NK cells. As a pleiotropic cytokine, IL-15 plays important roles in innate and adaptive immunity. Given its stimulatory effects on the adaptive and innate immune system, it is a potential candidate for use in immune oncology.

Consistent with its suppressive role, IL-10 has been previously reprted to inhibit IL-15-mediated T cell activation. However, as described hereafter, exposure of activated CD8+ T cells with PEG-IL-10 and IL-15 was associated with an increase in IFNγ secretion in at least an additive manner. These data suggest that, rather than inhibiting IL-15-mediated activation of T cells, treatment with PEG-IL-10 in combination with IL-15 results in enhanced activation. Thus, as described herein, the administration of a PEG-IL-10 in combination with an IL-15 agent under particular conditions has potential therapeutic implications that were not previously appreciated. Such combination therapy for the treatment of cancer-related conditions is a particular aspect of the present disclosure.

Human IL-10 is a homodimer, and each monomer comprises 178 amino acids, the first 18 of which comprise a signal peptide. Unless otherwise indicated, reference herein to human IL-10 refers to the mature form that lacks the signal peptide, wherein each monomer comprises 160 amino acids (see, e.g., U.S. Pat. No. 6,217,857). As used herein, the term "PEG-IL-10" refers to pegylated human IL-10 and variants thereof that exhibit activity comparable to the activity of mature human PEG-IL-10, such as pegylated murine IL-10 and pegylated forms of other IL-10 orthologs.

As used herein, the terms "IL-15", "IL-15 polypeptide(s)," "IL-15-agent(s)", "IL-15 molecule(s)" and the like are intended to be construed broadly and include, for example, human and non-human IL-15-related polypeptides, including homologs, variants (including muteins), and fragments thereof, as well as IL-15 polypeptides having, for example, a leader sequence (e.g., a signal peptide). Mature human IL-15 is a 114 amino acid monomeric polypeptide. Two transcripts have been reported, one with a 48 amino acid signal peptide (Long Signal Peptide; LSP) (FIG. 1A; SEQ ID NO:1), and the other with a 21 amino acid signal peptide (Short Signal Peptide; SSP) (FIG. 1B; SEQ ID NO:2), both of which produce the same mature protein (FIG. 1C; SEQ ID NO:3). In some embodiments, the present disclosure contemplates the use of the mature human IL-15 polypeptide (SEQ ID NO:3), whereas in other embodiments the present disclosure contemplates IL-15 polypeptides comprising the amino acid sequence of SEQ ID NO:3, wherein the polypeptides comprise at least one amino acid substitution, deletion or addition.

In particular embodiments, the present disclosure contemplates methods of treating or preventing a cancer-related disease, disorder or condition in a subject, comprising administering to the subject: a) a therapeutically effective amount of a PEG-IL-10, wherein the amount is sufficient to achieve a mean IL-10 serum trough concentration of at least 6.0 ng/mL; and b) a therapeutically effective amount of an IL-15 agent. In other embodiments, the present disclosure contemplates methods of treating or preventing a cancer-related disease, disorder or condition in a subject, comprising administering to the subject: a) a therapeutically effective amount of a PEG-IL-10, wherein the amount is sufficient to maintain a mean IL-10 serum trough concentration over a period of time, wherein the mean IL-10 serum trough concentration is at least 6.0 ng/mL, and wherein the mean IL-10 serum trough concentration is maintained for at least 90% of the period of time; and b) a therapeutically effective amount of an IL-15 agent. The methods of treating or preventing a cancer-related condition may be mediated by CD8+ T cells.

The desired IL-10 serum trough concentration may depend on a number of factors, including the nature of the disease, disorder or condition (e.g., localized tumor or metastatic disease), the extent to which the subject is suffering from the malady (e.g., early versus late stage disease), whether combination therapy is being administered, and patient-specific parameters (e.g., hepatic and renal function). By way of example, co-administration of PEG-IL-10 and a chemotherapeutic agent may only require a serum trough in the ~1-2 ng/mL range in order to observe clinical benefit, while metastatic cancer may require 6-10 ng/mL or more to achieve comparable clinical benefit (see, e.g., WO 2014/172392).

Thus, in particular embodiments of the present disclosure, the mean IL-10 serum trough concentration is at least 6.0 ng/mL, at least 7.0 ng/mL, at least 8.0 ng/mL, and least 9.0 ng/mL, at least 10.0 ng/mL, at least 11.0 ng/mL, at least 12.0 ng/mL, at least 13.0 ng/mL, at least 14.0 ng/mL, at least 15.0 ng/mL, at least 16.0 ng/mL, at least 17.0 ng/mL, at least 18.0 ng/mL, at least 19.0 ng/mL, at least 20.0 ng/mL, at least 21.0 ng/mL, at least 22.0 ng/mL, or greater than 22.0 ng/mL.

In other particular embodiments, the mean IL-10 serum trough concentration is at least 1.0 ng/mL, at least 1.5 ng/mL, at least 2.0 ng/mL, at least 2.5 ng/mL, at least 3.0 ng/mL, at least 3.5 ng/mL, at least 4.0 ng/mL, at least 4.5 ng/mL, at least 5.0 ng/mL, and least 5.5 ng/mL, at least 6.0 ng/mL, at least 6.5 ng/mL or greater than 7 ng/mL.

In further embodiments, the period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, or greater than 3 months.

In particular embodiments of the present disclosure, the mean IL-10 serum trough concentration is maintained for at least 85% of the period of time, at least 90%, at least 95%, at least 98%, at least 99% or 100% of the period of time.

It is envisaged that a dosing regimen sufficient to maintain a particular steady state serum trough concentration (e.g., 2.0 ng/mL) may result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (amount and frequency) are kept constant. After that period of time, the gradual but continual decrease ends and a steady state serum trough concentration is maintained.

By way of example, parenteral administration (e.g., SC and IV) of ~0.1 mg/kg/day of an IL-10 agent (e.g., mIL-10) to a mouse (e.g., a C57BL/6 mouse) is required to maintain a steady state serum trough concentration of, for example, 2.0 ng/mL. However, that steady state serum trough concentration may not be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of, for example, the approximately 30-day period, after which time the desired steady state serum trough concentration (e.g., 2.0 ng/mL) is maintained. One of skill in the art will be able to determine the dose needed to maintain the desired steady state trough concentration using, for example, ADME and patient-specific parameters.

Also envisaged are methods of treating or preventing a cancer-related disease, disorder or condition in a subject, comprising administering to the subject a therapeutically effective amount of a PEG-IL-10, wherein the amount is sufficient to achieve a mean IL-10 serum trough concentration of at least the EC50 of the PEG-IL-10. In other embodiments, the amount is sufficient to achieve a mean IL-10 serum trough concentration of at least the EC60, of at least the EC70, of at least the EC80, or of at least the EC90 of the PEG-IL-10.

As used herein, the term "EC50" and the phrase "half maximal effective concentration" have their generally accepted meaning; that is, the EC50 is the concentration of a therapeutic agent (e.g., a PEG-IL-10) which induces a response halfway between the baseline and the maximum after some specified exposure time. The skilled artisan is familiar with means for determining the EC50 of a therapeutic agent. For example, the EC50 may be determined using commercially available software (e.g., Graphpad Software, Inc.; La Jolla, Calif.) after measuring certain concentration-related parameters of the therapeutic agent in a cell-based assay.

A PEG-IL-10 of the present disclosure may comprise at least one PEG molecule covalently attached to at least one amino acid residue of at least one subunit of IL-10 or comprise a mixture of mono-pegylated and di-pegylated IL-10 in other embodiments. The PEG component of a PEG-IL-10 may have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

As indicated herein, the PEG-IL-10 is mature human PEG-IL-10 in some embodiments, while in other embodiments it is a variant of mature human PEG-IL-10 that exhibits activity comparable to the activity of mature human PEG-IL-10.

The present disclosure contemplates embodiments wherein the amount of the PEG-IL-10 component of the combination therapy that is administered to the subject to treat or prevent a cancer-related disease, disorder or condition is from 10.0 µg/kg/day to 20.0 µg/kg/day. In some embodiments, the amount of the PEG-IL-10 administered is from 12.0 µg/kg/day to 18.0 µg/kg/day.

According to the present disclosure, a PEG-IL-10 may be administered in combination with an IL-15 agent for the treatment of a cancer-related disease, disorder or condition in the subject. In some embodiments, the cancer is a solid tumor, such as a tumor associated with breast cancer, prostate cancer, lung cancer, liver cancer, pancreatic cancer, brain cancer, stomach cancer, ovarian cancer, kidney cancer, testicular cancer, and melanoma. In other embodiments, the cancer is a lymphoma, such as a B-cell lymphoma.

As indicated in the Experimental section, the therapeutic effects of the PEG-IL-10 and the IL-15 agent are additive in some embodiments, while they are synergistic in others.

A PEG-IL-10 and an IL-15 agent may be administered by any effective route. In some embodiments, they are administered by parenteral injection, including subcutaneous injection. In particular embodiments, a PEG-IL-10 is administered separately from the IL-15 agent, and in other embodiments a PEG-IL-10 and an IL-15 agent are administered together.

As noted above, the various types of IL-15 agents for use in the combination therapies of the present disclosure include human and non-human IL-15-related polypeptides, including homologs, variants (including muteins), and fragments thereof. In some embodiments, the IL-15 peptides have at least 60, at least 70, at least 80, at least 90, at least 95, at least 100, at least 101, at least 102, at least 103, at least 104, at least 105, at least 106, at least 107, at least 108, at least 109, at least 110, at least 111, at least 112, or at least 113 amino acid residues. In other embodiments, the IL-15 peptides have at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO:3.

In further embodiments the present disclosure contemplates IL-15 peptides having at least one amino acid substitution in at least one of the following regions of SEQ ID NO:3: amino acid residues 13-15, 17-29, 36-39, 51-58, 71-84, or 89-98. In other embodiments, the IL-15 peptides contemplated herein have at least one amino acid substitution in at least one of the following regions of SEQ ID NO:3: amino acid residues 17-28, 36-38, 51-57, 71-84, or 89-98. In still further embodiments, the IL-15 peptides have at least one amino acid substitution in at least one of the following positions of SEQ ID NO:3: 1, 3, 13-15, 17-29, 33, 34, 36-39, 41, 45, 46, 48, 49, 51-58, 60, 67, 71-84, 86, 87, 89-98, 101, 102, 104, 113, or 114, while in other embodiments the IL-15 peptides have at least one amino acid substitution in at least at one of the following positions of SEQ ID NO:3: 1, 17-28, 36-38, 41, 45, 46, 48, 49, 51-57, 60, 67, 71-84, 86, 87, 89-98, 101, 113, or 114.

As indicated herein, the IL-15 agent is mature human IL-15 in some embodiments, while in other embodiments the IL-15 agent is a variant of mature human IL-15 that exhibits activity comparable to the activity of mature human IL-15.

The present disclosure contemplates embodiments wherein the amount of the IL-15 component of the combination therapy that is administered to the subject to treat or prevent a cancer-related disease, disorder or condition is from 0.03 μg/kg/day to 3.0 μg/kg/day. In other embodiments, the amount of the IL-15 agent is from 0.03 μg/kg/day to 0.3 μg/kg/day, and in still other embodiments the amount of the IL-15 agent is from 1.0 μg/kg/day to 3.0 μg/kg/day.

In particular embodiments, the present disclosure contemplates dosing an IL-15 agent such that the serum concentration achieves a peak and is then cleared such that it is essentially unmeasurable before it is administered again. By way of example, when a PEG-IL-10 is administered every 24 hours to maintain a serum trough concentration of ~10 ng/mL, an 11-15 agent can be co-administered in an amount that results in a peak of approximately 15 ng/mL and then is metabolized within 12 hours, resulting in no measurable trough level for at least one-half of the dosing cycle. In order to avoid potential toxicities, dosing should be adjusted such that the IL-15 level does not exceed 20 ng/mL. As with administration of a PEG-IL-10, the dose of an IL-15 agent may depend on a number of factors, including the nature of the disease, disorder or condition (e.g., localized tumor or metastatic disease), the extent to which the subject is suffering from the malady (e.g., early versus late stage disease), whether combination therapy is being administered, and patient-specific parameters (e.g., hepatic and renal function).

The present disclosure includes pharmaceutical compositions comprising a PEG-IL-10 and an IL-15 agent as described herein, and a pharmaceutically acceptable diluent, carrier or excipient. In some embodiments, the PEG-IL-10 and the IL-15 agent are present in separate pharmaceutical compositions, each comprising a pharmaceutically acceptable diluent, carrier or excipient. In some embodiments, the excipient is an isotonic injection solution. The pharmaceutical compositions may be suitable for administration to a subject (e.g., a human), and may comprise one or more additional prophylactic or therapeutic agents. In certain embodiments, the pharmaceutical compositions are contained in one or more sterile containers (e.g., a single- or multi-use vial or a syringe). A kit may contain the sterile container(s), and the kit may also contain one or more additional sterile containers comprising at least one additional prophylactic or therapeutic agent or any other agent that may be used in pharmacological therapy. One or more additional prophylactic or therapeutic agents may be administered prior to, simultaneously with, or subsequent to the PEG-IL-10 and IL-15 agent.

Additional prophylactic or therapeutic agents (also referred to herein as supplementary agents and the like) that may be used with the methods of treating and/or preventing a cancer-related disease, disorder or condition include any agent that may provide some therapeutic benefit. By way of example, but not limitation, a prophylactic or therapeutic agent may be a chemotherapeutic agent, an immune- or inflammation-related agent, a metabolic agent, an antiviral agent or an anti-thrombotic agent. The methods of the present disclosure may also be used in combination with non-pharmacological agents (e.g., radiology).

In particular embodiments, the additional prophylactic or therapeutic agent is a chemotherapeutic agent, examples of which are set forth herein. In some embodiments, the chemotherapeutic agent is a platinum-based antineoplastic, also referred to as a platinum coordination complex. These platinum-based antineoplastic agents crosslink DNA, thereby inhibiting DNA repair and/or DNA synthesis in cancer cells. Examples of such agents include cisplatin, carboplatin, oxaliplatin, satraplatin, picoplatin, nedaplatin and triplatin.

Methods and models for optimizing dosing regimens for the PEG-IL-10 and IL-15 agents described herein are also contemplated by embodiments of the present disclosure. In other embodiments, the present disclosure contemplates methods for the identification of specific patient populations that are optimally suited for the combination therapies described herein. In some embodiments, the existence and/or extent of certain biomarkers can find utility in such methods.

Other aspects and embodiments will be apparent to the skilled artisan after reviewing the present disclosure.

BRIEF DESCRIPTION OF THE DRAWINGS

FIG. 1A depicts the IL-15 Long Signal Peptide (LSP) Protein (162 amino acid residues; SEQ ID NO:1). The signal peptide (underlined) comprises residues 1-48.

FIG. 1B depicts the IL-15 Short Signal peptide (SSP) Protein (135 amino acid residues; SEQ ID NO:2). The signal peptide (underlined) comprises residues 1-21.

FIG. 1C depicts the mature human IL-15 protein (114 amino acid residues) (SEQ ID NO:3).

FIG. 2A depicts the Long Signal Peptide (LSP) cDNA Open Reading Frame (ORF) (489 base pairs (SEQ ID NO:4), encoding 162 amino acid residues). The signal peptide (underlined) comprises base pairs 1-144, encoding the first 48 amino acids.

FIG. 2B depicts the Short Signal peptide (SSP) cDNA Open Reading Frame (ORF) (408 base pairs (SEQ ID NO:5), encoding 135 amino acid residues). The signal peptide (underlined) comprises base pairs 1-63, encoding the first 21 amino acids.

FIG. 2C depicts the nucleic acid sequence encoding mature human IL-15 Protein (345 base pairs (SEQ ID NO:6), encoding 114 amino acid residues).

DETAILED DESCRIPTION

Figure 3:
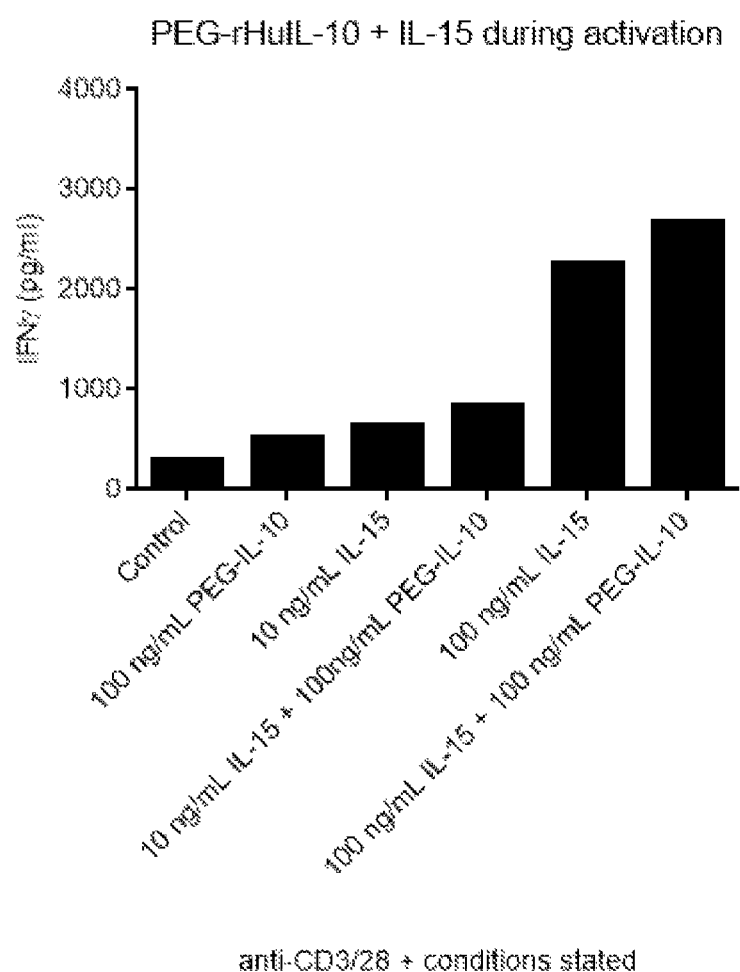
FIG. 3 indicates that exposure of CD8+ T cells during activation with anti-CD3/28 and PEG-rHuIL-10+ rHuIL-15 moderately enhanced INFγ secretion.
Figure 4:
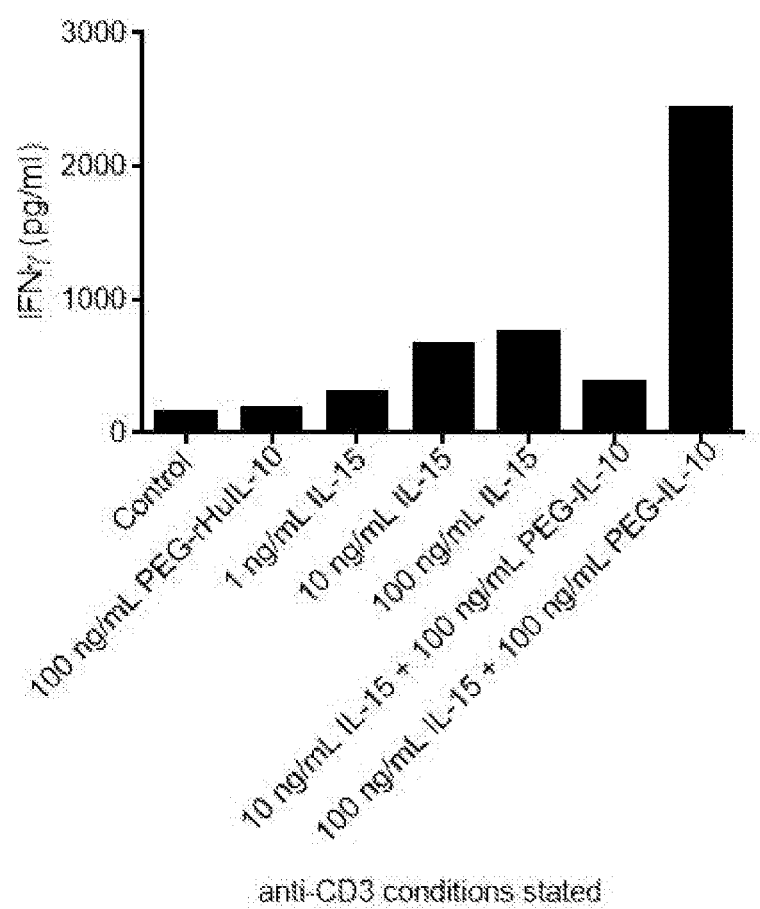
FIG. 4 indicates that exposure of CD8+ T cells during activation with anti-CD3 and PEG-hIL-10+ rHuIL-15 additively enhanced INFγ secretion.
Figure 5:
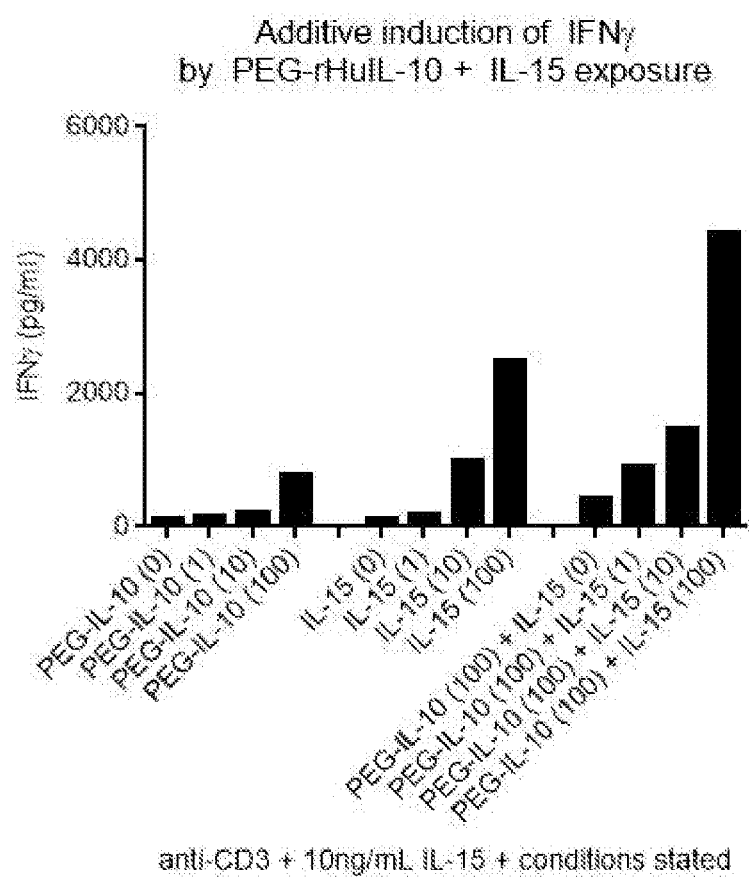
FIG. 5 indicates that exposure of CD8+ T cells activated with anti-CD3+ rHuIL-15, and then exposed during the rest phase to PEG-hIL-10+ rHuIL-15 at least additively enhanced INFγ secretion. The numbers in parentheses indicate concentration in ng/mL.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

In accordance with its suppressive role, IL-10 has been previously reported to inhibit IL-15-mediated T cell activation. However, as set forth in the Experimental section and described in detail herein, exposure of activated CD8+ T cells with PEG-IL-10 and IL-15 was associated with an increase in IFN-γ secretion in at least an additive manner. These data suggest that, rather than inhibiting IL-15-mediated activation of T cells, treatment with PEG-IL-10 in combination with IL-15 results in enhanced activation.

In view of that finding, the present disclosure contemplates methods of using a PEG-IL-10 (e.g., rHuPEG-IL-10), and compositions thereof, in combination with an IL-15 agent (e.g., rHuIL-15), and compositions thereof, for the treatment and/or prevention of cancer-related diseases, disorders and conditions, and/or the symptoms thereof. The methods comprise particular dosing regimens and provide the opportunity for additive or synergistic effects in the treatment and/or prevention of the disorders described herein.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it can correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule can be more permeable to cells, less susceptible to degradation, and less likely to elicit an immune response than large molecules.

The term "ligand" refers to, for example, peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor can be entirely intracellular, that is, it can reside in the cytosol, nucleus, or some other intracellular compartment. The complex of a ligand and receptor is termed a "ligand-receptor complex."

The terms "inhibitors" and "antagonists", or "activators" and "agonists", refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor can also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of a PEG-IL-10 (or the nucleic acid molecules encoding them), either directly or indirectly; or to enhance the ability of a molecule to produce an effect comparable to that of a PEG-IL-10. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator can act alone, or it can use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule can describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term can also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect can refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β-γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 dimer becomes biologically inactive upon disruption of the non-covalent interactions between the two monomer subunits.

As alluded to above, the terms "IL-10", "IL-10 polypeptide(s), "IL-10 molecule(s)", "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. The present disclosure contemplates pegylated forms of human IL-10 (NP 000563) and murine IL-10 (NP 034678), which exhibit 80% homology, and use thereof. In addition, the scope of the present disclosure includes pegylated IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

As used herein, the terms "pegylated IL-10", "PEG-IL-10" and the like refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. As used herein, the terms "dipegylated IL-10" and "di-PEG-IL-10" indicate that at least one polyethylene glycol molecule is attached to a single residue on each subunit of the IL-10 dimer, generally via a linker.

In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein.

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 peptide. In certain embodiments, the increase in half-life is greater than any decrease in biological activity. The biological activity of PEG-IL-10 is typically measured by assessing the levels of inflammatory cytokines (e.g., TNFα or IFNγ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some can be post-translational variants, e.g., glycosylated variants. The present disclosure contemplates the use of any pegylated variant of IL-10 provided it retains a suitable level of IL-10 activity.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates pegylated forms of active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide that can be pegylated can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length IL-10 peptide or polypeptide.

As discussed further below, the IL-10 polypeptides can be isolated from a natural source (e.g., an environment other than its naturally-occurring environment) and can also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Nucleic acid molecules encoding an IL-10 molecule contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

IL-15

Interleukin-15 (IL-15), also referred to as MGC9721, is a pro-inflammatory cytokine involved in the stimulation of cytolytic activity, cytokine secretion, and survival of NK cells, CD8+ memory T-cells and naïve CD8+ cells (see Fehniger, et al. (1999) J Immunol 162:4511-20). IL-15 induces the proliferation of naïve and memory CD4 and CD8+ T cells and NK cells (Sneller, M. C., et al. (2011) Blood 118(26):6845-48; Waldmann, T. A., et al. (2011) Blood 117(18):4787-95). In addition, IL-15 induces the secretion of IFN-γ, TNFα, IL-1β and IL-6 (Conlon, K. C., et al. (2015) J Clin Oncol 33(1):74-82; Berger, C., et al. (2009) Blood 114(12):2417-26) and enhances the cytotoxic function of both CD8+ T cells (Liu, K., et al. (2002) Proc Natl Acad Sci USA 99(9):6192-97; Wang, N. P., et al. (2002) Ann NY Acad Sci 975:46-56) and NK cells (Huntington, N. D., et al. (2009) J Exp Med 206(1):25-34).

As a pleiotropic cytokine, IL-15 plays important roles in innate and adaptive immunity (see Lodolce, et al. (December 2002) Cytokine Growth Factor Rev 13(6):429-39) and Alves, et al. (2003) Blood 102:2541-46). Given its stimulatory effects on the adaptive and innate immune system, it is a potential candidate for use in immune oncology.

IL-15 is constitutively expressed by a large number of cell types, including macrophages, monocytes, dendritic cells and fibroblasts (Grabstein, et al. (May 1994) Science 264 (5161):965-68). Expression of IL-15 can be stimulated by, for example, cytokines (e.g., GM-CSF), double-stranded mRNA, unmethylated CpG oligonucleotides, lipopolysaccharide through Toll-like receptors, and interferons (e.g., IFN-γ), or after infection of, for example, monocytes with herpes virus, *Mycobacterium tuberculosis* and *Candida albicans* (Bamford, et al. (May 1998) J Immunol 160(9):4418-26).

As discussed further below, IL-15 binds to a specific receptor complex on T-cells and NK cells. IL-15 and IL-15Rα are co-expressed on activated dendritic cells and on monocytes, and IL-15 functions in a complex with IL-15Rα (Bergamaschi, et al. (2008) J Biol Chem 283:4189-99). IL-15/IL-15α bind as a heterodimer to two chains on T-cells and NK cells—IL-2Rβ (also referred to as IL-15Rβ; CD122) and γc (also referred to as IL-2RG; CD132; γ-c; common γ-chain) molecules. The β and γc chains are shared between IL-2 and IL-15 and are essential for the signaling of these cytokines (Giri et al. (1994) EMBO J. 13:2822-30 and Giri et al. (1995) EMBO J. 14:3654-63).

Consistent with the sharing of the IL-2/IL-15βγc receptor complex, IL-15 has been shown to mediate many functions similar to those of IL-2 in vitro. They share many biological activities and exhibit similar contributions to the survival of T lymphocytes (see Waldmann, et al. (1999) Ann Rev Immunol 17:19-49). It is believed that the biological differences between IL-2 and IL-15 are likely due to, for example, their different production sites, their strength of association with membrane receptor proteins, termed IL-2α and IL-15Rα, respectively, and the regulation of these extra receptor molecules. IL-2 and IL-15 play a role in regulating the number of CD8+ memory cells.

IL-15 is predicted to be 12.8 kDa monomeric glycoprotein encoded by the 34 kb region on chromosome 4q31. IL-15 belongs to the four α-helix bundle family, other members of which include IL-2, IL-4, IL-7, IL-9, granulocyte colony-stimulating factor (G-CSF), and granulocyte-macrophage colony-stimulating factor (GM-CSF). The genomic structure of human IL-15 contains 9 exons (1-8 and 4A) and eight introns. Humans and mice share a similar intron/exon structure. The overall intron/exon structure of the portion of the IL-15 gene encoding the mature protein is similar to that of the IL-2 gene and other four α-helix bundle cytokines.

Those of skill in the art will appreciate that IL-15 nucleic acid and amino acid sequences are publicly available in gene databases (e.g., GenBank). As depicted in FIG. 1C (SEQ ID NO:3), the mature human IL-15 protein comprises 114 amino acid residues (12.8 kDA). The recombinant human IL-15 produced in *E. coli* is a single, non-glycosylated polypeptide chain (115 amino acid residues, including an N-terminal methionine, having a molecular mass of 12.9 kD). Two transcripts have been reported, both reportedly producing the same mature protein. Referring to FIG. 1A (SEQ ID NO:1), the IL-15 Long Signal Peptide (LSP) Protein (accession no. BC018149.2) comprises 162 amino acid residues, including a 48 residue signal peptide (underlined). Referring to FIG. 1B (SEQ ID NO:2), the IL-15 Short Signal peptide (SSP) Protein (accession no. BC100962.1) comprises 135 amino acid residues, including a 21 residue signal peptide (underlined). The LSP has been described as a secreted protein, and the SSP has been described as remaining intracellular.

FIG. 2A depicts the Long Signal Peptide (LSP) cDNA ORF (489 base pairs (SEQ ID NO:4), encoding 162 amino acid residues) (accession no. BC018149.2); the signal peptide (underlined) comprises base pairs 1-144, encoding the first 48 amino acids. FIG. 2B depicts the Short Signal peptide (SSP) cDNA ORF (408 base pairs (SEQ ID NO:5), encoding 135 amino acid residues) (accession no. BC100962.1); the signal peptide (underlined) comprises base pairs 1-63, encoding the first 21 amino acids. FIG. 2C depicts the nucleic acid sequence encoding mature human IL-15 Protein (345 base pairs (SEQ ID NO:6), encoding 114 amino acid residues).

Non-human exemplified mammalian IL-15 nucleic acid or amino acid sequences can be from, for example, primate, canine, feline, porcine, equine, bovine, ovine, rodentia, murine, rat, hamster, and guinea pig. Accession numbers for exemplified non-human mammalian IL-15 nucleic acid sequences include U19843 (macaque); DQ021912 (macaque); AB000555 (macaque); NM_214390 (porcine); DQ152967 (ovine); NM_174090 (bovine); NM_008357 (murine); NM_013129 (rattus); DQ083522 (water buffalo); XM_844053 (canine); DQ157452 (lagomorpha); and NM_001009207 (feline). Accession numbers for exemplified non-human mammalian IL-15 amino acid sequences include AAB60398 (macaque); AAY45895 (macaque); NP_999555 (porcine); NP_776515 (bovine); AAY83832 (water buffalo); ABB02300 (ovine); XP_849146 (canine); NP_001009207 (feline); NP_037261 (rattus); and NP_032383 (murine). The identity of mature cynomolygous monkey IL-15 ("cIL-15") compared to mature human IL-15 ("hIL-15") is 96%, while the identity of mature mouse IL-15 ("mIL-15") compared to mature hIL-15 is 75%.

Human IL-15 contains two disulfide bonds at positions C42-C88 and C35-C85, the former being homologous to the C—C within IL-2. There are two N-linked glycosylation sites at N79 and N112 (depending on the analytical method used, N71 may be deemed to be a third glycosylation site). The mature IL-15 protein has been predicted to have strong helical moments at amino acid residues 1 to 15, 18 to 57, 65 to 78, and 97 to 114, supporting its four α-helix bundle structure (Fehniger, et al. (Jan. 1, 2001) Blood 97(1)).

As indicated previously, a nexus exists between IL-15 and IL-2. Based upon complex regulation and differential patterns of IL-15 and IL-15Rα expression, it is likely that the critical in vivo functions of this receptor/ligand pair differ from those of IL-2 and IL-2Rα. IL-15 exhibits several key non-redundant roles, including its importance during natural killer (NK) cell, NK-T cell, and intestinal intraepithelial lymphocyte development and function. As IL-15 reportedly plays a role in autoimmune processes (e.g., rheumatoid arthritis) and malignancies (e.g., T-cell leukemia), disruptions in normal IL-15 function have been implicated in untoward effects in subjects.

Though both signal through the receptor subunit IL-2Rβ and the common γ-chain (γ(c)), IL-15 and IL-2 do not share all of the same biological functions. In the structure of the IL-15-IL-15Rα-IL-2Rβ-γ(c) quaternary complex, IL-15 binds to IL-2Rβ and γ(c) in a heterodimer resembling that of the IL-2-IL-2Rα-IL-2Rβ-γ(c) complex. IL-15Rα has been shown to substantially increase the affinity of IL-15 for IL-2Rβ, which, in turn, is required for IL-15 trans-signaling. IL-15 and IL-2 induce similar signals, and the specificity of IL-2Rα versus IL-15Rα has been shown to determine cellular responsiveness. (See Ring et al. (Dec. 13, 2012) Nat. Immunol. 13(12):1187-95).

IL-15 exists primarily as a membrane-bound form, although it also exists as a soluble molecule (Jakobisiak, et al. (April 2011) Cytokine Growth Factor Ref 22(2):99-109), and it is associated with two distinct signaling mechanisms. The primary mechanism is transpresentation which is mediated by membrane-bound complex IL-15/IL-15Rα. In this signaling mechanism, IL-15 binds to IL-15Rα receptor, with subsequent presentation to surrounding cells having the IL-15Rβγc complex on their cell surface. The second mechanism is cis-presentation, where IL 15 is presented by IL-15Rα to the 15Rβγc signaling complex on the same cell.

Referring to the primary signaling mechanism, upon binding of IL-15 to the IL-15Rα receptor and subsequent presentation to surrounding cells bearing IL-15Rβγc complex, the IL-15β subunit activates Janus kinase 1 (Jak1) and the γc subunit activates Janus kinase 2, which leads to phosphorylation and activation of signal transducer and activator of transcription 3 (STAT3) and STAT5. Because IL-15 and IL-2 share receptor subunits, they have similar downstream effects, including the induction of B-cell lymphoma (Bcl-2); mitogen-activated protein kinase (MAP) pathway, and the phosphorylation of lymphocyte-activated protein tyrosine kinase (Lck) and spleen tyrosine kinase (Syk), which results in cell proliferation and maturation (Schluns, et al. (August 2005) Int. J. Biochem. Cell Biol. 37(8):1567-71).

In contrast, the IL-15R signaling pathway in mast cells includes Jak2 and STAT5 instead Jak1/3 and STAT3/5. Phosphorylated STATs form transcription factors and activate transcription of appropriate genes. The β chain of IL-15R recruits and also activates protein tyrosine kinases of the Src family including Lck, Fyn and Lyn kinase. The β chain also activates phosphatidylinositol 3-kinase (PI3K) and AKT signaling pathways and induces expression of various transcription factors, including c-Fos, c-Jun, c-Myc and NF-κB (Jakobisiak, et al. (April 2011) Cytokine Growth Factor Ref 22(2):99-109).

Co-Administration of IL-10 and IL-15

As alluded to above, IL-10 is deemed to be an anti-inflammatory and immuno-suppressive cytokine that inhibits the secretion of IFN-γ, IL-12 (D'Andrea, A., et al. (1993) J Exp Med 178(3):1041-48), and TNFα (Armstrong, L., et al. (1996) Thorax 51(2):143-49). IL-10 also inhibits antigen presentation and subsequent activation of CD4+ T cells (de Waal Malefyt, R., et al. (1991) J Exp Med 174(5):1209-20; de Waal Malefyt, R., et al. (1991) J Exp Med 174(4):915-24) and is thus widely considered to be a potent immune suppressive cytokine.

Consistent with its suppressive role, IL-10 has been shown to inhibit IL-15-mediated T cell activation (Korholz, D., et al. (1997) Blood (90)11:4513-21). However, as set forth in the Experimental section, exposure of activated CD8+ T cells with PEG-IL-10 and IL-15 was associated with an increase in IFN-γ secretion in at least an additive manner. These data suggest that, rather than inhibiting IL-15-mediated activation of T cells, treatment with PEG-IL-10 in combination with IL-15 results in enhanced activation. Thus, as described herein the administration of PEG-IL-10 in combination with IL-15 under particular conditions has potential therapeutic implications that were not previously appreciated.

IL-15 engagement of the IL-15 receptor complex leads to phosphorylation of both STAT3 and STAT5 (Johnston, J. A., et al. (1995) Proc Natl Acad Sci USA 92(19):8705-09). Further investigation has revealed that IL-15 signaling also activates the PI3K pathway (Marzec, M., et al. (2008) Blood 111(4):2181-89; Nandagopal, N., et al. (2014) Front Immunol 5:187). This combination of signal transduction leads to the enhanced activation status and persistence of memory CD8+ T cells. In addition, IL-15 signaling, likely via its activation of the PI3K pathway, blocks the inhibitory signal derived from PD1/PDL1 interactions (Bennett, F., D. et al. (2003) J Immunol 170(2):711-18; Kinter, A. L., et al. (2008) J Immunol 181(10):6738-46).

Clinical investigation of PEGylated rHuIL-10 has unexpectedly revealed that IL-10's stimulation of the human immune system is far broader and Th1 polarizing than previously believed or accepted. Dosing with PEGylated rHuIL-10 leads to increases in serum IL-18, IFNγ, IL-4, IL-7 and GM-CSF. All of these cytokines have been shown to induce PD1, PDL1 or PDL2 (see, e.g, Li, B., A. et al. (2009) Clin Immunol 133(2):184-97; Terme, M., et al. (2011) Cancer Res71(16):5393-99).

Therefore, the unexpected finding that treatment with pegylated rHuIL-10 leads to a Th1 serum cytokine signature that likely induces PD1/PDL1-PDL2, and the results indicating that IL-15 can overcome the inhibitory effects of PD1/PDL1-PDL2 ligation indicates that combined treatment may synergistically inhibit tumor growth.

Serum Concentrations

The blood plasma levels of IL-10 in the methods described herein can be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, mean serum trough IL-10 concentrations have been found to be of particular import for efficacy in certain indications. Blood plasma levels of IL-15 referenced in the methods described herein can be characterized in a similar manner.

As set forth above, the desired IL-10 serum trough concentration may depend on a number of factors, including the nature of the disease, disorder or condition (e.g., localized tumor or metastatic disease), the extent to which the subject is suffering from the malady (e.g., early versus late stage disease), whether combination therapy is being administered, and patient-specific parameters (e.g., hepatic and renal function). By way of example, co-administration of PEG-IL-10 and a chemotherapeutic agent may only require a serum trough in the ~1-2 ng/mL range in order to observe clinical benefit, while metastatic cancer may require 6-10 ng/mL or more to achieve comparable clinical benefit.

In particular embodiments of the present disclosure, the mean IL-10 serum trough concentration is at least 6.0 ng/mL, at least 7.0 ng/mL, at least 8.0 ng/mL, and least 9.0 ng/mL, at least 10.0 ng/mL, at least 11.0 ng/mL, at least 12.0 ng/mL, at least 13.0 ng/mL, at least 14.0 ng/mL, at least 15.0 ng/mL, at least 16.0 ng/mL, at least 17.0 ng/mL, at least 18.0 ng/mL, at least 19.0 ng/mL, at least 20.0 ng/mL, at least 21.0 ng/mL, at least 22.0 ng/mL, or greater than 22.0 ng/mL.

In other particular embodiments, the mean IL-10 serum trough concentration is at least 1.0 ng/mL, at least 1.5 ng/mL, at least 2.0 ng/mL, at least 2.5 ng/mL, at least 3.0 ng/mL, at least 3.5 ng/mL, at least 4.0 ng/mL, at least 4.5 ng/mL, at least 5.0 ng/mL, and least 5.5 ng/mL, at least 6.0 ng/mL, at least 6.5 ng/mL or greater than 7 ng/mL.

In further embodiments, the period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, or greater than 3 months.

In particular embodiments of the present disclosure, the mean IL-10 serum trough concentration is maintained for at least 85% of the period of time, at least 90%, at least 95%, at least 98%, at least 99% or 100% of the period of time.

In still further embodiments of the present disclosure, blood plasma and/or serum level concentration profiles that can be produced include: a mean IL-10 plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL.

In particular embodiments of the present disclosure, a mean IL-10 serum trough concentration is in the range of from 1.0 pg/mL to 10 ng/mL. In some embodiments, the mean IL-10 serum trough concentration is in the range of from 1.0 pg/mL to 100 pg/mL. In other embodiments, the mean IL-10 serum trough concentration is in the range of from 0.1 ng/mL to 1.0 ng/mL. In still other embodiments, the mean IL-10 serum trough concentration is in the range of from 1.0 ng/mL to 10 ng/mL. It is to be understood that the present disclosure contemplates ranges incorporating any concentrations encompassed by those set forth herein even if such ranges are not explicitly recited. By way of example, the mean serum IL-10 concentration in an embodiment can be in the range of from 0.5 ng/mL to 5 ng/mL. By way of further examples, particular embodiments of the present disclosure comprise a mean IL-10 serum trough concentration in a range of from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL.

In particular embodiments, a mean IL-10 serum trough concentration of 1-2 ng/mL is maintained over the duration of treatment. The present disclosure also contemplates embodiments wherein the mean IL-10 serum peak concentration is less than or equal to about 10.0 ng/mL over the duration of treatment. Further embodiments contemplate a mean IL-10 serum trough concentration greater than or equal to about 10.0 ng/mL. The optimal mean serum concentration is generally that at which the desired therapeutic effect is achieved without introducing undesired adverse effects.

Certain embodiments of the present disclosure provide a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. In particular subject populations, a smaller peak-trough fluctuation indicates a lower probability that the subject will experience IL-10-related adverse effects. In addition, in some embodiments particular peak-trough fluctuations are determined for the treatment of particular diseases, disorders and conditions using particular dosing parameters, and those fluctuations are used as reference standards.

For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Thus, volume-of-distribution considerations are pertinent when assessing appropriate IL-10 dosing-related parameters. Moreover, efforts to target IL-10 agents to specific cell types have been explored (see, e.g., Rachmawati, H. (May 2007) Drug Met. Dist. 35(5):814-21), and the leveraging of IL-10 pharmacokinetic and dosing principles can prove invaluable to the success of such efforts.

The present disclosure contemplates administration of any dose and dosing regimen that results in maintenance of any of the IL-10 serum trough concentrations set forth above. By way of example, but not limitation, when the subject is a human, non-pegylated hIL-10 can be administered at a dose greater than 0.5 µg/kg/day, greater than 1.0 µg/kg/day, greater than 2.5 µg/kg/day, greater than 5 µg/kg/day, greater than 7.5 µg/kg, greater than 10.0 µg/kg, greater than 12.5 µg/kg, greater than 15 µg/kg/day, greater than 17.5 µg/kg/day, greater than 20 µg/kg/day, greater than 22.5 µg/kg/day, greater than 25 µg/kg/day, greater than 30 µg/kg/day, or greater than 35 µg/kg/day. In addition, by way of example, but not limitation, when the subject is a human, pegylated hIL-10 comprising a relatively small PEG (e.g., 5 kDa mono-di-PEG-hIL-10) can be administered at a dose greater than 0.5 µg/kg/day, greater than 0.75 µg/kg/day, greater than 1.0 µg/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 µg/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day.

The skilled artisan (e.g., a pharmacologist) is able to determine the optimum dosing regimen(s) when a PEG-IL-10 is administered in combination with an IL-15 agent. By way of example, in some embodiments the optimum PEG-IL-10 dosing regimen may require a reduction in the amount of PEG-IL-10 administered per dose (e.g., less than 1.0 µg/kg/day, less than 0.75 µg/kg/day, less than 0.5 µg/kg/day, less than 0.25 µg/kg/day, or less than 0.125 µg/kg/day). In certain exemplary embodiments of the present disclosure, a mean IL-10 serum trough concentration may be in a range of from about 0.1 ng/mL to about 9.5 ng/mL, from about 0.25 ng/mL to about 8.0 ng/mL, from about 0.5 ng/mL to about 7.0 ng/mL, from about 0.75 ng/mL to about 6.0 ng/mL, or from about 1.0 ng/mL to about 5.0 ng/mL.

The present disclosure contemplates dosing an IL-15 agent such that the serum concentration achieves a peak and is then cleared such that it is essentially unmeasurable before it is administered again. By way of example, when a PEG-IL-10 is administered every 24 hours to maintain a serum trough concentration of ~10 ng/mL, an 11-15 agent can be co-administered in an amount that results in a peak of approximately 15 ng/mL and then is metabolized within 12 hours, resulting in no measurable trough level for at least one-half of the dosing cycle. In order to avoid potential toxicities, dosing should be adjusted such that the IL-15 level does not exceed 20 ng/mL. As with administration of a PEG-IL-10, the dose of an IL-15 agent may depend on a number of factors, including the nature of the disease, disorder or condition (e.g., localized tumor or metastatic disease), the extent to which the subject is suffering from the malady (e.g., early versus late stage disease), whether combination therapy is being administered, and patient-specific parameters (e.g., hepatic and renal function).

When a PEG-IL-10 is administered in combination with an IL-15 agent such as those described herein, one or more of the dosing parameters of the PEG-IL-10 applicable to monotherapy can be modified while the dosing parameters of the IL-15 agent applicable to monotherapy can remain the same; one or more of the dosing parameters of the PEG-IL-10 applicable to monotherapy can remain the same while one or more of the dosing parameters of the IL-15 agent applicable to monotherapy can be modified; one or more of the dosing parameters of the PEG-IL-10 and the IL-15 agent applicable to monotherapy can be modified; or the dosing parameters of each of the PEG-IL-10 and the IL-15 agent can remain the same.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as 9-fluorenyl-methoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis can be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, dimethyl-2,6-dioxocyclohex-1-ylidene) ethyl (Dde), isopropyl, 4-methoxy-2,3-6-trimethylbenzyl-sulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or Tenta-Gel® derivatized with 5-(4'-aminomethyl)-3',5'-dimethoxy-phenoxy)valeric acid (PAL-anchor) or p-(2,4-dimethoxy-phenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluoro-phosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Nmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Nmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethyl sulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about –10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecyl-silylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide can be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH═CH— (cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C$_1$-C$_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from C$_1$-C$_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from C$_1$-C$_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, 6-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$-CO— or —(CH2)$_n$-C$_6$H$_4$—CO—) with functional groups which allow for the introduction of a bridge. Some examples are disulfides, disulfide mimetics such as the —(CH2)$_n$- carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:7); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:8); Transportan GWTLNSAGYLLGKINLKALAALAKKIL (SEQ ID NO:9); KALAWEAKLAKALAKALAKHLAKALAKALKCEA (SEQ ID NO:10); and RQIKIWFQNRRMKWKK (SEQ ID NO:11). Exemplary PTDs include, but are not limited to, YGRKKRRQRRR (SEQ ID NO:7), RKKRRQRRR (SEQ ID NO:12); an arginine homopolymer of from 3 arginine residues to 50 arginine residues; exemplary PTD domain amino acid sequences include, but are not limited to, any of the following: YGRKKRRQRRR (SEQ ID NO:7); RKKRRQRR (SEQ ID NO:13); YARAAARQARA (SEQ ID NO:14); THRLPRRRRRR (SEQ ID NO:15); and GGRRARRRRRR (SEQ ID NO:16).

The carboxyl group COR$_3$ of the amino acid at the C-terminal end of an IL-10 polypeptide can be present in a free form (R$_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C$_1$-C$_6$-alkyl alcohols, e.g., ethyl alcohol or tert-butanol. The carboxyl group can also be amidated with primary or secondary amines such as ammonia, branched or unbranched C$_1$-C$_6$-alkylamines or C$_1$-C$_6$ di-alkylamines, e.g., methylamine or dimethylamine.

The amino group of the amino acid NR$_1$R$_2$ at the N-terminus of an IL-10 polypeptide can be present in a free form (R$_1$=H and R$_2$=H) or in the form of a physiologically-tolerated salt such as, e.g., a chloride or acetate. The amino group can also be acetylated with acids such that R$_1$=H and R$_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which R$_1$ and/or R$_2$=C$_1$-C$_6$ alkyl or C$_2$-C$_8$ alkenyl or C$_7$-C$_9$ aralkyl. Alkyl residues can be straight-chained, branched or cyclic (e.g., ethyl, isopropyl and cyclohexyl, respectively).

Pegylation of IL-10

Pegylation of IL-10 comprises conjugating or linking the IL-10 polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself can enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula R(O—CH$_2$—CH$_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography can be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114; and Miron and Wilcheck (1993) Bio-conjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on certain molecules (e.g., IFN-α) has been shown to be a hydrolytically unstable imidazolecarbamate linkage (see, e.g., Lee and McNemar, U.S. Pat. No. 5,985,263). Second generation pegylation technology has been designed to avoid these unstable linkages as well as the lack of selectivity in residue reactivity. Use of a PEG-aldehyde linker targets a single site on the N-terminus of a polypeptide through reductive amination.

PEG can be bound to a polypeptide of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide. Another activated polyethylene glycol which can be bound to a free amino group is 2,4-bis(O-methoxypolyethyleneglycol)-6-chloro-s-triazine, which can be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Linkers: Linkers and their use have been described above. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-alanine polymers, alanine-serine polymers, glycine-serine polymers (for example, $(G_mS_o)_n$, $(GSGGS)_n$ (SEQ ID NO:26), $(G_mS_oG_m)_n$, $(G_mS_oG_mS_oG_m)_n$ (SEQ ID NO:17), $(GSGGS_m)_n$ (SEQ ID NO:18), $(GSGS_mG)_n$ (SEQ ID NO:19) and $(GGGS_m)_n$ (SEQ ID NO:20), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Examples of flexible linkers include, but are not limited to GGSG (SEQ ID NO:21), GGSGG (SEQ ID NO:22), GSGSG (SEQ ID NO:17), GSGGG (SEQ ID NO:23), GGGSG (SEQ ID NO:24), and GSSSG (SEQ ID NO:25).

Additional examples of flexible linkers include glycine polymers (G)n or glycine-serine polymers (e.g., (GS)n, (GSGGS)n (SEQ ID NO:26), (GGGS)n (SEQ ID NO:27) and (GGGGS)n (SEQ ID NO:28), where n=1 to 50, for example, 1, 2, 3, 4, 5, 6, 7, 8, 9, 10, 10-20, 20-30, 30-50). Exemplary flexible linkers include, but are not limited to GGGS (SEQ ID NO:20), GGGGS (SEQ ID NO:28), GGSG (SEQ ID NO:21), GGSGG (SEQ ID NO:22), GSGSG (SEQ ID NO:17), GSGGG (SEQ ID NO:23), GGGSG (SEQ ID NO:24), and GSSSG (SEQ ID NO:25). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein.

Therapeutic and Prophylactic Uses

In particular embodiments, the present disclosure contemplates the use of a PEG-IL-10 and an IL-15 agent in the treatment and/or prevention of cancer-related diseases, disorders or conditions. While particular uses are described in detail hereafter, it is to be understood that the present disclosure is not so limited.

Representative cancers that may be treated or prevented using the combination therapies disclosed herein include cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the the immune system (e.g., spleen or thymus).

The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, myelomas, sarcomas, teratocarcinomas, chemically-induced cancers, and metastasis. In particular embodiments, the tumor or cancer is colon cancer, ovarian cancer, breast cancer, melanoma, lung cancer, or glioblastoma.

As described elsewhere herein, in some embodiments the present disclosure provides methods for treating a cancer-related disease, disorder or condition with a PEG-IL-10 and an IL-15 agent in combination with at least one additional therapeutic or diagnostic agent, examples of which are provided herein.

Pharmaceutical Compositions

The PEG-IL-10 and IL-15 agents contemplated by the present disclosure can be in the form of compositions suitable for administration to a subject. In general, such compositions are "pharmaceutical compositions" comprising PEG-IL-10 and/or an IL-15 agent and one or more pharmaceutically acceptable or physiologically acceptable diluents, carriers or excipients. In certain embodiments, the PEG-IL-10 and IL-15 agents are each present in a therapeutically acceptable amount. The pharmaceutical compositions can be used in the methods of the present disclosure; thus, for example, the pharmaceutical compositions can be administered ex vivo or in vivo to a subject in order to practice the therapeutic and prophylactic methods and uses described herein.

In the description of the pharmaceutical compositions, and aspects thereof, that follows, the pharmaceutical compositions are generally described in the context of a PEG-IL-10. However, it is to be understood that the description also applies to the IL-15 agents of the present disclosure, either in pharmaceutical compositions comprising combinations of a PEG-IL-10 and an IL-15 agent, or in pharmaceutical compositions comprising only one of the components.

The pharmaceutical compositions of the present disclosure can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of a PEG-IL-10 and/or an IL-15 agent contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver a PEG-IL-10 or an IL-15 agent, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient can be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active ingredient of an agent co-administered with a PEG-IL-10 and/or an IL-15 agent described herein is in a form suitable for oral use. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The PEG-IL-10 and IL-15 agents contemplated by the present disclosure can be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the PEG-IL-10 and IL-15 agents, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, can also be utilized to release the polypeptides disclosed herein over a defined period of time.

Particular embodiments of the present disclosure contemplate parenteral administration. The parenteral administration is intravenous in some embodiments and is subcutaneous in others.

Supplementary Combination Therapy

The present disclosure contemplates the use of the combinations of PEG-IL-10 and an IL-15 agent in further combination with one or more active therapeutic agents or other prophylactic or therapeutic modalities (e.g., radiation). For purposes of this application, such further combinations are sometimes referred to as "supplementary combinations", "supplementary combination therapy", "combinations with an additional prophylactic or therapeutic agent" and the like, and agents that are added to combinations of PEG-IL-10 and an IL-15 agent can be referred to as "supplementary agents" and the like. In such supplementary combination therapy, the various supplementary active agent(s) frequently have different mechanisms of action than a PEG-IL-10 and/or an IL-15 agent. Such supplementary combination therapy can be especially advantageous by allowing a dose reduction of one or more of the agents, thereby reducing or eliminating the adverse effects associated with one or more of the agents; furthermore, such supplementary combination therapy can have a synergistic therapeutic or prophylactic effect on the underlying proliferative disease, disorder, or condition. In some embodiments of the present disclosure the supplementary agent(s) is a diagnostic agent(s).

In particular embodiments, the present disclosure provides methods for treating and/or preventing cancer-related diseases, disorders or conditions with a PEG-IL-10 and an IL-15 agent, and at least one additional therapeutic or diagnostic agent.

In some embodiments of the present disclosure, each of the PEG-IL-10, the IL-15 agent and the supplementary agent(s) can be in a separate dosage form. By way of example, the PEG-IL-10 can be in a formulation suitable for SC administration, the IL-15 agent can be in a formulation suitable for IV administration, and the supplementary agent can be in a formulation suitable for oral administration; in this context, each of the agents can be housed separately or two or more of the agents can be housed together (e.g., as distinct components of a kit). In other embodiments of the present disclosure, two or more of the PEG-IL-10, the IL-15 agent and the supplementary agent(s) are in the same dosage form. For example, the PEG-IL-10, the IL-15 agent, and the supplementary agent(s) can be formulated for IV administration; in this context, one or more of the agents can be co-formulated (e.g., as the active therapeutic agents in a syringe).

In certain embodiments, the PEG-IL-10, the IL-15 agent, and the supplemental agent(s) (e.g., a chemotherapeutic agent) are administered or applied sequentially, e.g., where the PEG-IL-10 is administered first, an IL-15 agent is administered second, and a supplemental agent is administered last. In other embodiments, the PEG-IL-10, the IL-15 agent, and the supplemental agent(s) are administered simultaneously, e.g., where two of them are administered simultaneously and the third is administered either before or after. Regardless of whether the PEG-IL-10, the IL-15 agent, and the supplemental agent(s) are administered sequentially, simultaneously, or some variation thereof, they are considered to be administered as supplementary combination therapy for purposes of the present disclosure.

The present disclosure contemplates the use of any possible dosing regimen for the supplementary combination therapy that may be acceptable, appropriate or optimal under the circumstances. The regimens described hereafter are exemplary, not exclusionary. In one embodiment, treatment with the PEG-IL-10, an IL-15 agent, and the supplemental agent(s) are maintained over a period of time. In another embodiment, treatment with the PEG-IL-10, an IL-15 agent, and the supplemental agent(s) are reduced or continued over a period to time (e.g., when the subject is stable). In another embodiment, treatment with the supplemental agent(s) is reduced or discontinued (e.g., when the subject is stable), while treatment with the PEG-IL-10 and an IL-15 agent is maintained at a constant dosing regimen. In a further embodiment, treatment with the supplemental agent(s) is reduced or discontinued (e.g., when the subject is stable), treatment with the PEG-IL-10 is reduced (e.g., lower dose, less frequent dosing or shorter treatment regimen), and treatment with the IL-15 agent is maintained at a constant dosing regimen. In a further embodiment, treatment with the supplemental agent(s) is reduced or discontinued (e.g., when the subject is stable), treatment with the PEG-IL-10 is reduced (e.g., lower dose, less frequent dosing or shorter treatment regimen), and treatment with IL-15 agent is maintained at a constant dosing regimen.

In yet another embodiment, treatment with the supplemental agent(s) and the PEG-IL-10 is maintained at a constant dosing regimen, while treatment with the IL-15 agent is reduced or discontinued (e.g., when the subject is stable). In yet a further embodiment, treatment with the supplemental agent(s) and the IL-15 agent is maintained at a constant dosing regimen, while treatment with the PEG-IL-10 is reduced or discontinued (e.g., lower dose, less frequent dosing or shorter treatment regimen). Identification and use of other dosing regimens will be apparent to the skilled artisan.

While particular agents suitable for use with the combinations of a PEG-IL-10 and an IL-15 agent disclosed herein are set forth hereafter, it is to be understood that the present disclosure is not so limited. By way of example, but not limitation, a prophylactic or therapeutic agent may be a chemotherapeutic agent, an immune- or inflammation-related agent, a metabolic agent, an antiviral agent or an anti-thrombotic agent. The methods of the present disclosure may also be used in combination with non-pharmacological agents (e.g., radiology).

In a particular embodiment, the present disclosure contemplates the use of a PEG-IL-10 and an IL-15 agent with a chemotherapeutic agent(s) for treating and/or preventing cancer, tumor, or precancerous or cancer-associated disease, disorder or condition. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophsphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Any other agent useful in the treatment or prevention of the cancerous conditions described herein is contemplated as a supplementary agent, including, but not limited to, a cytokine or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

In particular embodiments, the additional prophylactic or therapeutic agent is a chemotherapeutic agent, examples of which are set forth herein. In some embodiments, the chemotherapeutic agent is a platinum-based antineoplastic, also referred to as a platinum coordination complex. These platinum-based antineoplastic agents crosslink DNA, thereby inhibiting DNA repair and/or DNA synthesis in cancer cells. Examples of such agents include cisplatin, carboplatin, oxaliplatin, satraplatin, picoplatin, nedaplatin and triplatin The present disclosure encompasses pharmaceutically acceptable salts, acids or derivatives of any of the above.

Dosing

A PEG-IL-10 and an IL-15 agent of the present disclosure can be administered to a subject in an amount that is dependent upon, for example, the goal of the administration (e.g., the degree of resolution desired); the age, weight, sex, and health and physical condition of the subject the formulation being administered; the route of administration; and the nature of the disease, disorder, condition or symptom thereof. The dosing regimen can also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

As discussed elsewhere herein, the present disclosure contemplates embodiments wherein a PEG-IL-10 is administered in an amount and frequency such that a desired serum trough concentration (e.g., ≥10 ng/mL) is maintained. Embodiments are also contemplated wherein an IL-15 agent is dosed such that the serum concentration achieves a peak and is then cleared to an unmeasurable level before it is administered again.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

In addition, an effective dose of a PEG-IL-10 and an IL-15 agent of the present disclosure can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The amount of a PEG-IL-10 and an IL-15 agent necessary to treat a disease, disorder or condition described herein can be determined by activity assays known in the art. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of TNFα or IFNγ in biological samples.

The therapeutically effective amount of PEG-IL-10 can range from about 0.01 to about 100 μg protein/kg of body weight/day, from about 0.1 to 20 μg protein/kg of body weight/day, from about 0.5 to 10 μg protein/kg of body weight/day, or about 1 to 4 μg protein/kg of body weight/day. The present disclosure contemplates embodiments wherein the amount of the PEG-IL-10 component of the combination therapy is from 10.0 μg/kg/day to 20.0 μg/kg/day. In some embodiments, the amount of the PEG-IL-10 administered is from 12.0 μg/kg/day to 18.0 μg/kg/day.

In some embodiments, PEG-IL-10 is administered by continuous infusion to delivery about 50 to 800 μg protein/kg of body weight/day (e.g., about 1 to 16 μg protein/kg of body weight/day of PEG-IL-10). The infusion rate can be varied based on evaluation of, for example, adverse effects and blood cell counts. Other specific dosing parameters for a PEG-IL-10 are described elsewhere herein. The present disclosure contemplates embodiments wherein the amount of the IL-15 component of the combination therapy that is administered to the subject to treat or prevent a cancer-related disease, disorder or condition is from 0.01 μg/kg/day to 10.0 μg/kg/day. In other embodiments, the amount of the IL-15 agent is from 0.1 μg/kg/day to 10.0 μg/kg/day, and in still other embodiments the amount of the IL-15 agent is from 1.0 μg/kg/day to 10.0 μg/kg/day. In still further embodiments, the amount of the IL-15 component of the combination therapy that is administered to the subject to treat or prevent a cancer-related disease, disorder or condition is from 0.1 μg/kg/day to 15.0 μg/kg/day. In other embodiments, the amount of the IL-15 agent is from 1.0 μg/kg/day to 15.0 μg/kg/day, and in still other embodiments the amount of the IL-15 agent is from 10.0 μg/kg/day to 15.0 μg/kg/day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the disclosed PEG-IL-10 and/or IL-15 agent is contained in a "unit dosage form". The phrase "unit dosage form" refers to physically discrete units, each unit containing a predetermined amount of a PEG-IL-10 and/or an IL-15 agent of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising PEG-IL-10 and/or an IL-15 agent, and pharmaceutical compositions thereof. The kits are generally in the form of a physical structure housing various components, as described below, and can be utilized, for example, in practicing the methods described above. One or more components of a kit can be in a sterile container (e.g., a sterile vial).

A kit can include a PEG-IL-10 and/or an IL-15 agent disclosed herein, which can be in the form of a pharmaceutical composition suitable for administration to a subject. The PEG-IL-10 and/or IL-15 agent can be provided in a form that is ready for use or in a form requiring, for example, reconstitution or dilution prior to administration. When the PEG-IL-10 and/or IL-15 agent is in a form that needs to be reconstituted by a user, the kit can also include buffers, pharmaceutically acceptable excipients, and the like, packaged with or separately from the PEG-IL-10 and/or IL-15 agent. A kit can also contain both the PEG-IL-10 and an IL-15 agent as described herein; the kit can contain the several agents separately or they can already be combined in the kit. Similarly, when supplementary therapy (e.g., a PEG-IL-10, an IL-15 agent, and a supplementary agent) is contemplated, the kit can contain the several agents separately or two or more of them can already be combined in the kit. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.). Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: s or sec=second(s); min=minute(s); h or hr=hour(s); aa=amino acid(s); bp=base pair(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; nM=nanomolar; μM=micromolar; mM=millimolar; M=molar; kDa=kilodalton; i.m.=intramuscular(ly);

i.p.=intraperitoneal(ly); SC or SQ=subcutaneous(ly); HPLC=high performance liquid chromatography; BW=body weight; U=unit; ns=not statistically significant; PMA=Phorbol 12-myristate 13-acetate; PBS=phosphate-buffered saline; HSA=human serum albumin; DMEM=Dulbeco's Modification of Eagle's Medium; PBMCs=primary peripheral blood mononuclear cells; FBS=fetal bovine serum; FCS=fetal calf serum; HEPES=4-(2-hydroxyethyl)-1-piperazineethanesulfonic acid; LPS=lipopolysaccharide; ATCC=American Type Culture Collection.

Materials and Methods.

The following general materials and methods were used, where indicated, or can be used in the Examples below:

Molecular Biology Procedures.

Standard methods in molecular biology are described in the scientific literature (see, e.g., Sambrook and Russell (2001) Molecular Cloning, $3^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

Antibody-Related Processes.

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.). Further discussion of antibodies appears elsewhere herein.

Software.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, N.V.).

Pegylation.

Pegylated IL-10 as described herein can be synthesized by any means known to the skilled artisan. Exemplary synthetic schemes for producing mono-PEG-IL-10 and a mix of mono-/di-PEG-IL-10 have been described (see, e.g., U.S. Pat. No. 7,052,686; US Pat. Publn. No. 2011/0250163; WO 2010/077853). Particular embodiments of the present disclosure comprise a mix of selectively pegylated mono- and di-PEG-IL-10. In addition to leveraging her own skills in the production and use of PEGs (and other drug delivery technologies) suitable in the practice of the present disclosure, the skilled artisan is familiar with many commercial suppliers of PEG-related technologies (e.g., NOF America Corp (Irvine, Calif.) and Parchem (New Rochelle, N.Y.)).

Mice.

Various mice and other animal strains can be used in conjunction with the teachings of the present disclosure. For example, immunocompetent Balb/C or B-cell-deficient Balb/C mice can be obtained from The Jackson Lab., Bar Harbor, Me. and used in accordance with standard procedures (see, e.g., Martin et al (2001) Infect. Immun., 69(11): 7067-73 and Compton et al. (2004) Comp. Med. 54(6):681-89). Other mice strains suitable for the experimental work contemplated by the present disclosure are known to the skilled artisan and are generally available from The Jackson Lab or another supplier.

IL-10 Concentrations.

Serum IL-10 concentration levels and exposure levels can be determined by standard methods used in the art. For example, a serum exposure level assay can be performed by collecting whole blood (~50 µL/mouse) from mouse tail snips into plain capillary tubes, separating serum and blood cells by centrifugation, and determining IL-10 exposure levels by standard ELISA kits and techniques.

The assays described hereafter are representative, and not exclusionary.

In Vitro Cytokine Secretion Assay.

Activated primary human CD8+ T-cells secrete IFN-γ when treated with PEG-IL-10 and then with an anti-CD3 antibody. The following protocol provides an exemplary assay to examine cytokine secretion.

Human PBMCs can be isolated according to any standard protocol (see, e.g., Fuss et al. (2009) Current Protocols in Immunology, Unit 7.1, John Wiley, Inc., NY). CD8+ T-cells can be isolated using Miltenyi Biotec's MACS cell separation technology according to the manufacture's protocol (Miltenyi Biotec; Auburn, Calif.). For assays during activation, the isolated CD8+ T-cells ($2 \times 10^6$ cells/mL, $5 \times 10^5$ cells per well of a standard 96-well plate) can be activated with plate-bound anti-CD3 and anti-CD28 (plates are pre-coated with 10 µg/mL anti-CD3 and 2 µg/mL anti-CD28; Affymetrix eBioscience; San Diego, Calif.) and appropriate concentrations of IL-15 or PEG-IL-10 for 3 days in AIM V media (Life Technologies; Carlsbad, Calif.). The media can then be collected and assayed for IFN-γ using a commercially available ELISA kit following the manufacture's protocol (Affymetrix eBioscience; San Diego, Calif.). For assays during the rest phase, the isolated CD8+ T-cells ($3 \times 10^6$ cells/mL, $3 \times 10^6$ cells per well of a standard 24-well plate) can be activated with plate-bound anti-CD3 and anti-CD28 (plates are pre-coated with 10 µg/mL anti-CD3 and 2 µg/mL anti-CD28; Affymetrix eBioscience; San Diego, Calif.) for 3 days. Following activation, cells can then be collected, re-plated ($2 \times 10^6$ cells/mL, $5 \times 10^5$ cells per well of a standard 96-well plate) and treated with appropriate concentrations of IL-15 or PEG-hIL-10 for 3 days in AIM V media. After treatment, cells can be collected, re-plated ($2 \times 10^6$ cells/mL, $5 \times 10^5$ cells per well of a standard 96-well plate) and treated with 1 µg/mL soluble anti-CD3 for 4 hrs in AIM V media. The media can then be collected and assayed for IFN-γ (Affymetrix eBioscience; San Diego, Calif.), Granzyme B and Perforin (Mabtech; Cincinnati, Ohio) using commercially available ELISA kits following the manufacture's protocol.

TNFα Inhibition Assay.

PMA-stimulation of U937 cells (lymphoblast human cell line from lung available from Sigma-Aldrich (#85011440); St. Louis, Mo.) causes the cells to secrete TNFα, and subsequent treatment of these TNFα-secreting cells with human IL-10 causes a decrease in TNFα secretion in a dose-dependent manner. An exemplary TNFα inhibition assay can be performed using the following protocol.

After culturing U937 cells in RMPI containing 10% FBS/FCS and antibiotics, plate $1 \times 105$, 90% viable U937 cells in 96-well flat bottom plates (any plasma-treated tissue culture plates (e.g., Nunc; Thermo Scientific, USA) can be used) in triplicate per condition. Plate cells to provide for the following conditions (all in at least triplicate; for 'media alone' the number of wells is doubled because one-half will be used for viability after incubation with 10 nM PMA): 5 ng/mL LPS alone; 5 ng/mL LPS+0.1 ng/mL rhIL-10; 5 ng/mL LPS+1 ng/mL rhIL-10; 5 ng/mL LPS+10 ng/mL rhIL-10; 5 ng/mL LPS+100 ng/mL rhIL-10; 5 ng/mL LPS+ 1000 ng/mL rhIL-10; 5 ng/mL LPS+0.1 ng/mL PEG-rhIL-10; 5 ng/mL LPS+1 ng/mL PEG-rhIL-10; 5 ng/mL LPS+10 ng/mL PEG-rhIL-10; 5 ng/mL LPS+100 ng/mL PEG-rhIL-10; and 5 ng/mL LPS+1000 ng/mL PEG-rhIL-10. Expose each well to 10 nM PMA in 200 μL for 24 hours, culturing at 37° C. in 5% $CO_2$ incubator, after which time ~90% of cells should be adherent. The three extra wells can be re-suspended, and the cells are counted to assess viability (>90% should be viable). Wash gently but thoroughly 3× with fresh, non-PMA-containing media, ensuring that cells are still in the wells. Add 100 μL per well of media containing the appropriate concentrations (2× as the volume will be diluted by 100%) of rhIL-10 or PEG-rhIL-10, incubate at 37° C. in a 5% $CO_2$ incubator for 30 minutes. Add 100 μL per well of 10 ng/mL stock LPS to achieve a final concentration of 5 ng/mL LPS in each well, and incubate at 37° C. in a 5% $CO_2$ incubator for 18-24 hours. Remove supernatant and perform TNFα ELISA according to the manufacturer's instructions. Run each conditioned supernatant in duplicate in ELISA.

MC/9 Cell Proliferation Assay.

IL-10 administration to MC/9 cells (murine cell line with characteristics of mast cells available from Cell Signaling Technology; Danvers, Mass.) causes increased cell proliferation in a dose-dependent manner. Thompson-Snipes, L. et al. (1991) J. Exp. Med. 173:507-10) describe a standard assay protocol in which MC/9 cells are supplemented with IL3+IL-10 and IL-3+IL-4+IL-10. Vendors (e.g., R&D Systems, USA; and Cell Signaling Technology, Danvers, Mass.) use the assay as a lot release assay for rhIL-10. Those of ordinary skill in the art will be able to modify the standard assay protocol described in Thompson-Snipes, L. et al, such that cells are only supplemented with IL-10.

Tumor Models and Tumor Analysis.

Any art-accepted tumor model, assay, and the like can be used to evaluate the effect of the IL-10 molecules described herein on various tumors. The tumor models and tumor analyses described hereafter are representative of those that can be utilized. Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B-cell deficient Balb/C mice can be used. PEG 10-mIL-10 can be administered to the immunocompetent mice, while PEG-hIL-10 treatment can be in the B-cell deficient mice. Tumors are allowed to reach a size of 100-250 mm³ before treatment is started. IL-10, PEG-mIL-10, PEG-hIL-10, or buffer control is administered SC at a site distant from the tumor implantation. Tumor growth is typically monitored twice weekly using electronic calipers. Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C. Primary tumor growth is typically monitored twice weekly using electronic calipers. Tumor volume can be calculated using the formula (width×length/2) where length is the longer dimension. Tumors are allowed to reach a size of 90-250 mm³ before treatment is started.

Example 1

Effect of PEG-IL-10 in Combination with IL-15

Activated primary human CD8+ T-cells secrete IFN-γ when treated with PEG-IL-10 and then with an anti-CD3 antibody. In order to mimic the conditions a T cell would encounter during antigen presentation by a dendritic cell, CD8+ T cells were exposed to anti-CD³/anti-CD28 co-stimulation in the presence of PEG-IL-10, IL-15, or a combination of both. As indicated in FIG. 3, INFγ secretion was moderately enhanced when CD8+ T cells were exposed to PEG-IL-10+IL-15 during activation with anti-CD³/anti-CD28 compared to INFγ secretion observed when CD8+ T cells were exposed to either agent alone. The data set forth in FIG. 3, as well as that presented in FIGS. 4-7, was generated using PEG-rHuIL-10 and rHuIL-15.

In order to mimic the conditions a T cell would encounter during antigen presentation without co-stimulation, CD8+ T cells were exposed to anti-CD3 in the presence of PEG-IL-10, IL-15, or a combination of both. As set forth in FIG. 4, the combination of PEG-IL-10 and IL-15 surprisingly resulted in at least additive and potentially synergistic enhancement of INFγ secretion.

Figure 6:
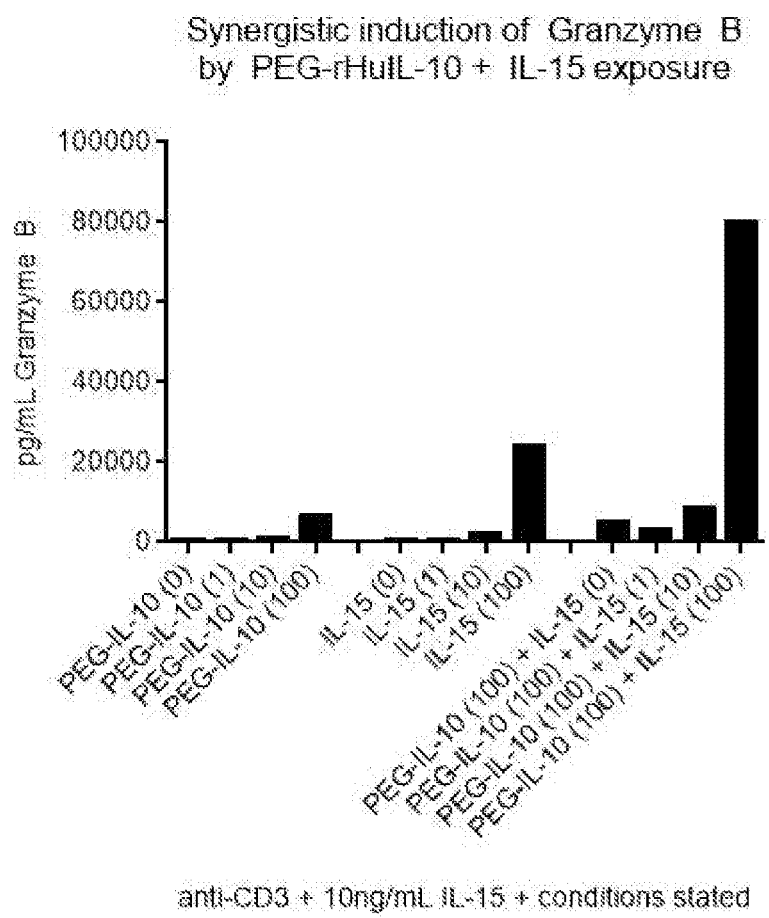
FIG. 6 indicates that exposure of CD8+ T cells activated with anti-CD3+ rHuIL-15, and then exposed to PEG-hIL-10+ rHuIL-15 during the rest phase synergistically enhanced Granzyme B secretion. The numbers in parentheses indicate concentration in ng/mL.
Figure 7:
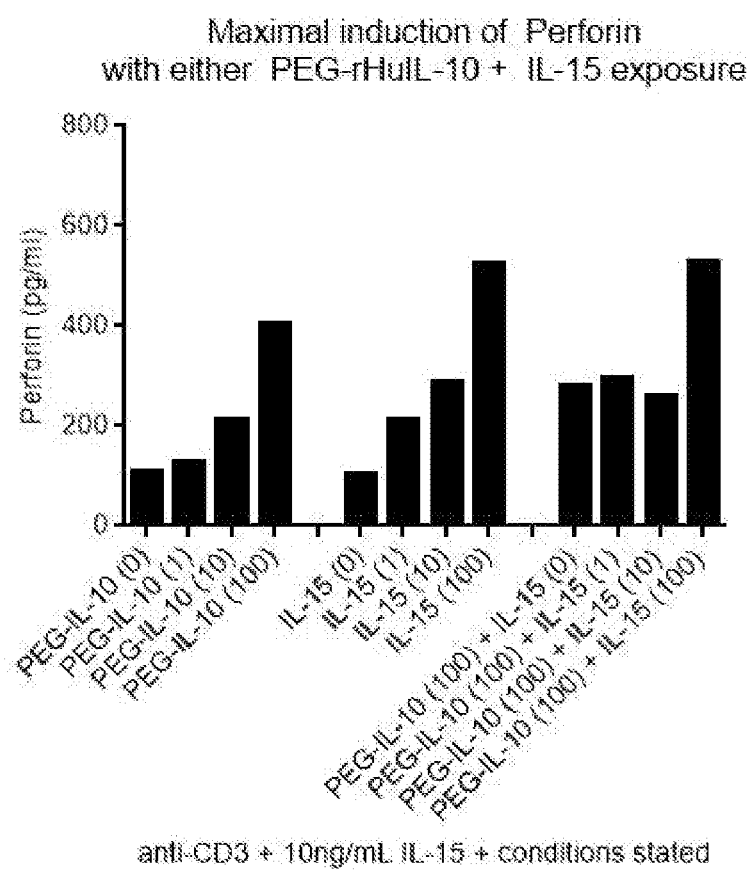
FIG. 7 indicates that exposure of CD8+ T cells activated with anti-CD3+ rHuIL-15, and then exposed to PEG-rHuIL-10+ rHuIL-15 during the rest phase maximally induced Perforin secretion. The numbers in parentheses indicate concentration in ng/mL.

IL-10 (e.g., PEG-IL-10) has been shown to directly activate the cytotoxicity of human and murine CD8+ T cells through the direct upregulation of the cytotoxic enzymes granzyme A, granzyme B, and perforin. In addition, under appropriate conditions, exposure of these cells to IL-10 enhances the intracellular accumulation of IFN-γ, which can be secreted upon T-cell receptor ligation with soluble anti-CD3 or cognate MHC I loaded with peptide antigen. In order to mimic the environment that a previously-activated T cell would encounter within a tumor, CD8+ T cells were activated by exposure to anti-CD3 and IL-15 for three days, then rested for 3 days with PEG-IL-10 and IL-15. Under these conditions CD8+ T cells exhibited at least an additive and potentially synergistic enhancement of INFγ secretion (FIG. 5) and synergistic induction of Granzyme B (FIG. 6). Furthermore, under these conditions exposure to either cytokine alone resulted in maximal induction of Perforin (FIG. 7).

Figure 8:
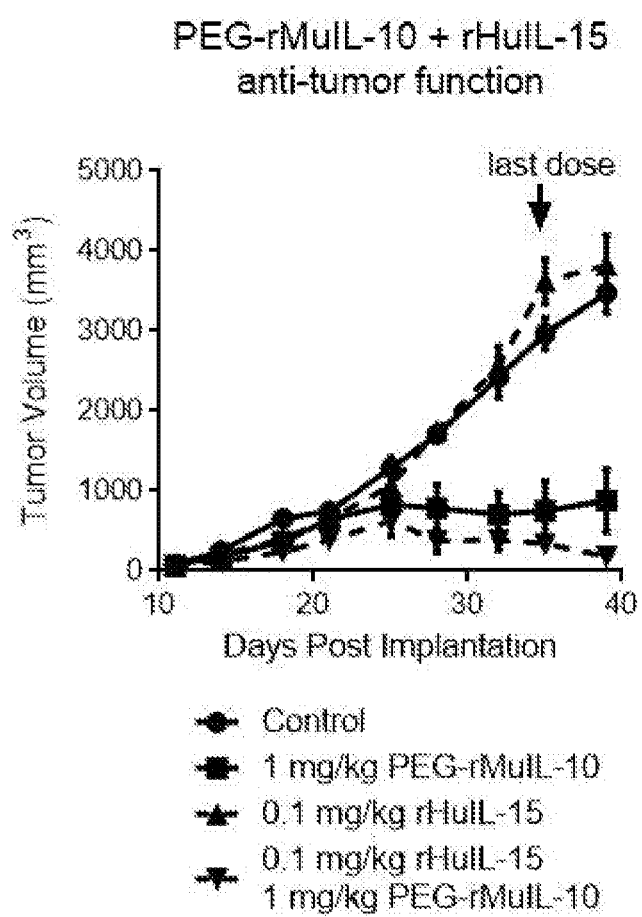
FIG. 8 indicates that PEG-rMuIL-10 and rHuIL-15 at least additively combined to control the growth of 4T1 tumors in mice.

The in vivo combination of PEG-rMuIL-10 and rHuIL-15 was evaluated in a 4T1 mammary carcinoma model. The model that is highly tumorigenic and invasive and can spontaneously metastasize from the primary tumor in the mammary gland to multiple distant sites including lymph nodes, blood, liver, lung, brain, and bone (Pulaski, V A and Ostrand-Rosenberg, S (May 2001) Curr Protoc Immunol Chapter 20:Unit 20.2). As indicated in FIG. 8, the combination had at least an additive therapeutic effect in controlling the growth of 4T1 tumors in mice. Given the aggressive nature of this model's primary tumor growth and metastatic capacity, it is possible that these data can be extrapolated to other models, suggesting that the combined anti-tumor efficacy will translate to other breast, colon, melanoma and squamous cell carcinomas.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

The invention claimed is:

1. A method of treating cancer in a human subject, comprising administering to the human subject:
   a) a therapeutically effective amount of a PEG-IL-10 agent, wherein the amount of the PEG-IL-10 agent is from 0.1 µg/kg to 20.0 µg/kg, wherein the PEG-IL-10 agent is mature human PEG-IL-10, and wherein the PEG component of the PEG-IL-10 agent is covalently attached via a linker to the alpha amino group of the amino acid residue at the N-terminus of at least one subunit of the PEG-IL-10 agent; and
   b) a therapeutically effective amount of an IL-15 agent, wherein the IL-15 agent comprises mature human IL-15.

2. The method of claim 1, wherein the PEG-IL-10 agent is administered to the subject at least once daily.

3. The method of claim 1, wherein the PEG-IL-10 agent is administered to the subject at least once every 72 hours.

4. The method of claim 1, wherein the PEG-IL-10 agent comprises a mixture of mono-pegylated and di-pegylated IL-10.

5. The method of claim 1, wherein the PEG component of the PEG-IL-10 agent has a molecular mass from about 5 kDa to about 20 kDa.

6. The method of claim 1, wherein the administering is by parenteral injection.

7. The method of claim 6, wherein the parenteral injection is subcutaneous or intravenous.

8. The method of claim 1, wherein the amount of the PEG-IL-10 is from 0.5 µg/kg/day to 10 µg/kg/day.

9. The method of claim 1, wherein the amount of the IL-15 agent is from 0.01 µg/kg/day to 10.0 µg/kg/day.

10. The method of claim 9, wherein the amount of the IL-15 agent is from 0.1 µg/kg/day to 10.0 µg/kg/day.

11. The method of claim 9, wherein the amount of the IL-15 agent is from 1.0 µg/kg/day to 10.0 µg/kg/day.

12. The method of claim 1, wherein the cancer is a solid tumor.

13. The method of claim 12, wherein the solid tumor is selected from the group consisting of breast cancer, prostate cancer, lung cancer, liver cancer, pancreatic cancer, brain cancer, stomach cancer, ovarian cancer, kidney cancer, testicular cancer, and melanoma.

14. The method of claim 1, wherein the cancer is a lymphoma.

15. The method of claim 14, wherein the lymphoma is a B-cell lymphoma.

16. The method of claim 1, further comprising administering at least one additional prophylactic or therapeutic agent.

17. The method of claim 16, wherein an additional prophylactic or therapeutic agent is a chemotherapeutic agent.

18. The method of claim 17, wherein the chemotherapeutic agent is a platinum-based antineoplastic agent.

19. The method of claim 1, wherein the PEG-IL-10 agent is recombinantly made in bacteria.

20. The method of claim 1, wherein the IL-15 agent is recombinantly made in bacteria.

* * * * *

SEQUENCE LISTING

```
<160> NUMBER OF SEQ ID NOS: 28

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 135
<212> TYPE: PRT
<213> ORGANISM: Homo sapiens

<400> SEQUENCE: 2

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95
```

Ser Asn Gly Asn Val Thr Glu Ser Gly Cys Lys Glu Cys Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
        130                 135

<210> SEQ ID NO 3
<211> LENGTH: 114
<212> TYPE: PRT
<213> ORGANISM: Homo sapiens

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 4
<211> LENGTH: 489
<212> TYPE: DNA
<213> ORGANISM: Homo sapiens

<400> SEQUENCE: 4
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca agtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag     420 gaaaaaaata ttaagaatt tttgcagagt tttgtacata ttgtccaaat gttcatcaac     480
acttcttga                                                            489

<210> SEQ ID NO 5
<211> LENGTH: 408
<212> TYPE: DNA
<213> ORGANISM: Homo sapiens

<400> SEQUENCE: 5
atggtattgg gaaccataga tttgtgcagc tgtttcagtg cagggcttcc taaaacagaa      60
gccaactggg tgaatgtaat aagtgatttg aaaaaaattg aagatcttat tcaatctatg     120
catattgatg ctactttata tacggaaagt gatgttcacc ccagttgcaa agtaacagca     180

```
atgaagtgct tctcttgga gttacaagtt atttcacttg agtccggaga tgcaagtatt    240
catgatacag tagaaaatct gatcatccta gcaaacaaca gtttgtcttc taatgggaat    300
gtaacagaat ctggatgcaa agaatgtgag gaactggagg aaaaaaatat taagaatttt    360
ttgcagagtt ttgtacatat tgtccaaatg ttcatcaaca cttcttga                408
```

<210> SEQ ID NO 6
<211> LENGTH: 345
<212> TYPE: DNA
<213> ORGANISM: Homo sapiens

<400> SEQUENCE: 6

```
aactgggtga atgtaataag tgatttgaaa aaaattgaag atcttattca atctatgcat     60
attgatgcta ctttatatac ggaaagtgat gttcaccccca gttgcaaagt aacagcaatg    120
aagtgctttc tcttggagtt acaagttatt tcacttgagt ccggagatgc aagtattcat    180
gatacagtag aaaatctgat catcctagca acaacagttt gtcttctaa tgggaatgta     240 acagaatctg gatgcaaaga atgtgaggaa ctggaggaaa aaatattaa gaatttttg      300 cagagttttg tacatattgt ccaaatgttc atcaacactt cttga                    345
```

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide sequence

<400> SEQUENCE: 7

Tyr Gly Arg Lys Lys Arg Arg Gln Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide sequence

<400> SEQUENCE: 8

Arg Arg Gln Arg Arg Thr Ser Lys Leu Met Lys Arg
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Synthetic polypeptide sequence

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic polypeptide sequence

```
<400> SEQUENCE: 10

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide sequence

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide sequence

<400> SEQUENCE: 12

Arg Lys Lys Arg Arg Gln Arg Arg Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide sequence

<400> SEQUENCE: 13

Arg Lys Lys Arg Arg Gln Arg Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide sequence

<400> SEQUENCE: 14

Tyr Ala Arg Ala Ala Ala Arg Gln Ala Arg Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic polypeptide sequence

<400> SEQUENCE: 15

Thr His Arg Leu Pro Arg Arg Arg Arg Arg
1               5                   10

<210> SEQ ID NO 16
<211> LENGTH: 11
<212> TYPE: PRT
```

```
<213> ORGANISM: Artificial Sequence
<220> FEATURE:
<223> OTHER INFORMATION: Synthetic polypeptide sequence

<400> SEQUENCE: 16

Gly Gly Arg Arg Ala Arg Arg Arg Arg Arg
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(1)
<223> OTHER INFORMATION: This residue may be repeated up to 20 times.
<220> FEATURE:
<221> NAME/KEY: MISC_FEATURE
<222> LOCATION: (1)..(5)
<223> OTHER INFORMATION: This stretch of residues may be repeated up to
      20 times.
<220> FEATURE:
<221> NAME/KEY: MISC_FEATURE
<222> LOCATION: (2)..(2)
<223> OTHER INFORMATION: This residue may be repeated up to 20 times.
<220> FEATURE:
<221> NAME/KEY: MISC_FEATURE
<222> LOCATION: (3)..(3)
<223> OTHER INFORMATION: This residue may be repeated up to 20 times.
<220> FEATURE:
<221> NAME/KEY: MISC_FEATURE
<222> LOCATION: (4)..(4)
<223> OTHER INFORMATION: This residue may be repeated up to 20 times.
<220> FEATURE:
<221> NAME/KEY: MISC_FEATURE
<222> LOCATION: (5)..(5)
<223> OTHER INFORMATION: This residue may be repeated up to 20 times.

<400> SEQUENCE: 17

Gly Ser Gly Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: This stretch of residues may be repeated up to
      20 times.
<220> FEATURE:
<221> NAME/KEY: MISC_FEATURE
<222> LOCATION: (5)..(5)
<223> OTHER INFORMATION: This residue may be repeated up to 20 times.

<400> SEQUENCE: 18

Gly Ser Gly Gly Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
```

```
<223> OTHER INFORMATION: This stretch of residues may be repeated up to
      20 times.
<220> FEATURE:
<221> NAME/KEY: MISC_FEATURE
<222> LOCATION: (4)..(4)
<223> OTHER INFORMATION: This residue may be repeated up to 20 times.

<400> SEQUENCE: 19

Gly Ser Gly Ser Gly
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(4)
<223> OTHER INFORMATION: This stretch of residues may be repeated up to
      20 times.
<220> FEATURE:
<221> NAME/KEY: MISC_FEATURE
<222> LOCATION: (4)..(4)
<223> OTHER INFORMATION: This residue may be repeated up to 20 times.

<400> SEQUENCE: 20

Gly Gly Gly Ser
1

<210> SEQ ID NO 21
<211> LENGTH: 4
<212> TYPE: PRT
<213> ORGANISM: Artificial Sequence
<220> FEATURE:
<223> OTHER INFORMATION: Synthetic polypeptide sequence

<400> SEQUENCE: 21

Gly Gly Ser Gly
1

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide sequence

<400> SEQUENCE: 22

Gly Gly Ser Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide sequence

<400> SEQUENCE: 23

Gly Ser Gly Gly Gly
1               5

<210> SEQ ID NO 24
<211> LENGTH: 5
<212> TYPE: PRT
<213> ORGANISM: Artificial Sequence
<220> FEATURE:
```

```
<223> OTHER INFORMATION: Synthetic polypeptide sequence

<400> SEQUENCE: 24

Gly Gly Gly Ser Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide sequence

<400> SEQUENCE: 25

Gly Ser Ser Ser Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: This stretch of residues may be repeated up to
      50 times.

<400> SEQUENCE: 26

Gly Ser Gly Gly Ser
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(4)
<223> OTHER INFORMATION: This stretch of residues may be repeated up to
      50 times.

<400> SEQUENCE: 27

Gly Gly Gly Ser
1

<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide sequence
<220> FEATURE:
<221> NAME/KEY: MISC_FEATURE
<222> LOCATION: (1)..(5)
<223> OTHER INFORMATION: This stretch of residues may be repeated up to
      50 times.

<400> SEQUENCE: 28

Gly Gly Gly Gly Ser
1               5
```